(12) United States Patent
Nelson

(10) Patent No.: US 9,080,145 B2
(45) Date of Patent: Jul. 14, 2015

(54) SINGLE PLURIPOTENT STEM CELL CULTURE

(75) Inventor: Shelley Nelson, Skillman, NJ (US)

(73) Assignee: LifeScan Corporation, Milpitas, CA (US)

( * ) Notice: Subject to any disclaimer, the term of this patent is extended or adjusted under 35 U.S.C. 154(b) by 773 days.

(21) Appl. No.: 12/164,795

(22) Filed: Jun. 30, 2008

(65) Prior Publication Data

US 2009/0325294 A1 Dec. 31, 2009

Related U.S. Application Data

(60) Provisional application No. 60/947,444, filed on Jul. 1, 2007.

(51) Int. Cl.
*C12N 5/00* (2006.01)
*C12N 5/02* (2006.01)
*C12N 5/0735* (2010.01)
*C12N 5/071* (2010.01)

(52) U.S. Cl.
CPC ............ *C12N 5/0068* (2013.01); *C12N 5/0606* (2013.01); *C12N 5/0608* (2013.01); *C12N 2501/115* (2013.01); *C12N 2501/119* (2013.01); *C12N 2501/16* (2013.01); *C12N 2501/385* (2013.01); *C12N 2501/41* (2013.01); *C12N 2501/415* (2013.01); *C12N 2501/70* (2013.01)

(58) Field of Classification Search
CPC ...................................................... C12N 5/0068
USPC .......................................................... 435/380
See application file for complete search history.

(56) References Cited

U.S. PATENT DOCUMENTS

| | | |
|---|---|---|
| 3,209,652 A | 10/1965 | Burgsmueller |
| 3,845,641 A | 11/1974 | Waller |
| 3,935,067 A | 1/1976 | Thayer |
| 4,499,802 A | 2/1985 | Simpson |
| 4,537,773 A | 8/1985 | Shenvi |
| 4,557,264 A | 12/1985 | Hinsch |
| 4,737,578 A | 4/1988 | Evans et al. |
| 5,215,893 A | 6/1993 | Mason et al. |
| 5,449,383 A | 9/1995 | Chatelier et al. |
| 5,525,488 A | 6/1996 | Mason et al. |
| 5,567,612 A | 10/1996 | Vacanti |
| 5,665,568 A | 9/1997 | Mason et al. |
| 5,686,090 A | 11/1997 | Schilder et al. |
| 5,713,957 A | 2/1998 | Steele et al. |
| 5,716,810 A | 2/1998 | Mason et al. |
| 5,718,922 A | 2/1998 | Herrero-Vanrell |
| 5,759,830 A | 6/1998 | Vacanti |
| 5,770,417 A | 6/1998 | Vacanti |
| 5,780,454 A | 7/1998 | Adams et al. |
| 5,834,308 A | 11/1998 | Peck et al. |
| 5,843,780 A | 12/1998 | Thomson |
| 5,908,782 A | 6/1999 | Marshank et al. |
| 5,914,262 A | 6/1999 | MacMichael et al. |
| 5,942,435 A | 8/1999 | Wheeler |
| 6,001,647 A | 12/1999 | Peck et al. |
| 6,022,743 A | 2/2000 | Naughton |
| 6,083,903 A | 7/2000 | Adams et al. |
| 6,087,113 A | 7/2000 | Caplan et al. |
| 6,200,806 B1 | 3/2001 | Thomson |
| 6,261,549 B1 | 7/2001 | Fernandez et al. |
| 6,281,012 B1 | 8/2001 | McIntosh et al. |
| 6,297,217 B1 | 10/2001 | Adams et al. |
| 6,306,424 B1 | 10/2001 | Vyakarnam |
| 6,328,960 B1 | 12/2001 | McIntosh et al. |
| 6,331,298 B1 | 12/2001 | Ferguson |
| 6,333,029 B1 | 12/2001 | Vyakarnam |
| 6,365,149 B2 | 4/2002 | Vyakarnam |
| 6,436,704 B1 | 8/2002 | Roberts et al. |
| 6,458,589 B1 | 10/2002 | Rambhatla et al. |
| 6,458,593 B1 | 10/2002 | Musick et al. |
| 6,509,369 B2 | 1/2003 | Scott |
| 6,521,427 B1 | 2/2003 | Evans |
| 6,534,084 B1 | 3/2003 | Vyakarnam |
| 6,599,323 B2 | 7/2003 | Melican |
| 6,617,152 B2 | 9/2003 | Bryhan et al. |
| 6,617,317 B1 | 9/2003 | Adams et al. |
| 6,626,950 B2 | 9/2003 | Brown |
| 6,642,048 B2 | 11/2003 | Xu et al. |
| 6,656,488 B2 | 12/2003 | Yi |
| 6,670,127 B2 | 12/2003 | Evans |
| 6,703,017 B1 | 3/2004 | Peck et al. |
| 6,713,446 B2 | 3/2004 | Gupta |
| 6,793,945 B2 | 9/2004 | Bathurst |
| 6,800,480 B1 | 10/2004 | Bodnar et al. |
| 6,815,203 B1 | 11/2004 | Bonner-Weir et al. |
| 6,958,319 B2 | 10/2005 | Gupta |
| 6,987,110 B2 | 1/2006 | Zhang et al. |

(Continued)

FOREIGN PATENT DOCUMENTS

| | | |
|---|---|---|
| CN | 1389565 A | 7/2002 |
| CN | 101092606 A | 12/2007 |
| EP | 0363125 A2 | 4/1990 |
| EP | 348969 B1 | 5/1993 |
| EP | 0617126 B1 | 9/1994 |
| EP | 0800829 B1 | 10/1997 |
| EP | 92302 B1 | 11/2006 |
| EP | 1873237 | 1/2008 |
| EP | 1391505 B1 | 1/2009 |
| KR | 10-2008-0020098 A | 3/2008 |

(Continued)

OTHER PUBLICATIONS

Lim et al. Proteomics, 2:1187-1203, 2002.*

(Continued)

*Primary Examiner* — Valarie Bertoglio
(74) *Attorney, Agent, or Firm* — Lois A. Gianneschi

(57) ABSTRACT

The present invention relates to the field of pluripotent stem cell culture and methods facilitate pluripotent stem cell culture at industrial levels.

25 Claims, 14 Drawing Sheets

(56) References Cited

U.S. PATENT DOCUMENTS

| | | |
|---|---|---|
| 7,005,252 B1 | 2/2006 | Thomson et al. |
| 7,033,831 B2 | 4/2006 | Fisk et al. |
| 7,157,275 B2 | 1/2007 | Guarino et al. |
| 7,297,539 B2 | 11/2007 | Mandalam et al. |
| 7,326,572 B2 | 2/2008 | Fisk et al. |
| 7,371,576 B2 | 5/2008 | Tsang et al. |
| 7,410,798 B2 | 8/2008 | Mandalam et al. |
| 7,413,734 B2 | 8/2008 | Mistry et al. |
| 7,442,548 B2 | 10/2008 | Thomson et al. |
| 7,449,334 B2 | 11/2008 | Thomsom et al. |
| 7,510,876 B2 | 3/2009 | D'Amour et al. |
| 7,534,608 B2 | 5/2009 | Martinson et al. |
| 7,569,385 B2 | 8/2009 | Haas |
| 7,585,672 B2 | 9/2009 | Odorico et al. |
| 7,704,738 B2 | 4/2010 | D'Amour et al. |
| 7,993,920 B2 | 8/2011 | Martinson et al. |
| 8,187,878 B2 | 5/2012 | Dalton et al. |
| 2002/0072117 A1 | 6/2002 | Xu et al. |
| 2003/0082155 A1 | 5/2003 | Habener et al. |
| 2003/0138948 A1 | 7/2003 | Fisk |
| 2003/0180903 A1 | 9/2003 | Bryhan et al. |
| 2004/0015805 A1 | 1/2004 | Kidd et al. |
| 2004/0058412 A1 | 3/2004 | Ho et al. |
| 2004/0062753 A1 | 4/2004 | Rezania |
| 2004/0106196 A1 | 6/2004 | Fraser et al. |
| 2004/0121460 A1 | 6/2004 | Lumelsky et al. |
| 2004/0121461 A1 | 6/2004 | Honmou et al. |
| 2004/0132729 A1 | 7/2004 | Salituro et al. |
| 2004/0161419 A1 | 8/2004 | Strom et al. |
| 2004/0171623 A1 | 9/2004 | Reynolds |
| 2004/0209901 A1 | 10/2004 | Adams |
| 2004/0220393 A1 | 11/2004 | Ward |
| 2004/0241761 A1 | 12/2004 | Sarvetnick et al. |
| 2005/0037488 A1 | 2/2005 | Mitalipova et al. |
| 2005/0037491 A1 | 2/2005 | Mistry et al. |
| 2005/0053588 A1 | 3/2005 | Yin et al. |
| 2005/0054093 A1 | 3/2005 | Haas |
| 2005/0054098 A1 | 3/2005 | Mistry et al. |
| 2005/0054102 A1 | 3/2005 | Wobus et al. |
| 2005/0058631 A1 | 3/2005 | Kihm et al. |
| 2005/0063961 A1 | 3/2005 | Friedlander et al. |
| 2005/0148070 A1 | 7/2005 | Thomson |
| 2005/0158852 A1 | 7/2005 | Wang |
| 2005/0158853 A1 | 7/2005 | D'Amour et al. |
| 2005/0187298 A1 | 8/2005 | Vasudevan et al. |
| 2005/0208029 A1 | 9/2005 | Umezawa et al. |
| 2005/0233446 A1 | 10/2005 | Parsons et al. |
| 2005/0244962 A1 | 11/2005 | Thomson |
| 2005/0260749 A1 | 11/2005 | Odorico et al. |
| 2005/0266554 A1 | 12/2005 | D'Amour et al. |
| 2006/0003446 A1 | 1/2006 | Keller et al. |
| 2006/0030042 A1 | 2/2006 | Brivaniou et al. |
| 2006/0040387 A1 | 2/2006 | Fisk et al. |
| 2006/0148081 A1 | 7/2006 | Kelly et al. |
| 2006/0194315 A1* | 8/2006 | Condie et al. .................. 435/366 |
| 2006/0194321 A1 | 8/2006 | Colman et al. |
| 2006/0281174 A1 | 12/2006 | Xu et al. |
| 2007/0001001 A1 | 1/2007 | Myers et al. |
| 2007/0082397 A1 | 4/2007 | Hasson et al. |
| 2007/0154981 A1 | 7/2007 | Hori et al. |
| 2007/0155661 A1 | 7/2007 | Kim |
| 2007/0254359 A1 | 11/2007 | Rezania |
| 2007/0259421 A1 | 11/2007 | D'Amour et al. |
| 2007/0259423 A1 | 11/2007 | Odorico et al. |
| 2007/0264713 A1 | 11/2007 | Terstegge et al. |
| 2008/0091234 A1 | 4/2008 | Kladakis et al. |
| 2008/0241107 A1 | 10/2008 | Copland, III et al. |
| 2008/0268533 A1 | 10/2008 | Dalton et al. |
| 2008/0268534 A1 | 10/2008 | Robins et al. |
| 2009/0093055 A1 | 4/2009 | Fisk et al. |
| 2009/0170198 A1 | 7/2009 | Rezania |
| 2009/0203141 A1 | 8/2009 | Lin et al. |
| 2009/0298178 A1 | 12/2009 | D'Amour |
| 2010/0003749 A1 | 1/2010 | Uchida et al. |
| 2010/0015100 A1 | 1/2010 | Xu |
| 2010/0015711 A1 | 1/2010 | Davis et al. |
| 2010/0093053 A1 | 4/2010 | Oh et al. |
| 2010/0112693 A1 | 5/2010 | Rezania et al. |
| 2012/0045830 A1 | 2/2012 | Green et al. |

FOREIGN PATENT DOCUMENTS

| | | |
|---|---|---|
| WO | 9219759 A2 | 2/1992 |
| WO | 9847892 A1 | 10/1998 |
| WO | WO 99/20741 A1 | 4/1999 |
| WO | 0029549 A1 | 5/2000 |
| WO | WO 01/51616 A2 | 7/2001 |
| WO | WO 01/81549 | 11/2001 |
| WO | 0246183 A2 | 6/2002 |
| WO | 0246197 A1 | 6/2002 |
| WO | 02092756 A2 | 11/2002 |
| WO | 03026584 A2 | 4/2003 |
| WO | 03033697 A1 | 4/2003 |
| WO | 03042405 A2 | 5/2003 |
| WO | 0305049 A1 | 6/2003 |
| WO | 03054169 A1 | 7/2003 |
| WO | 03062405 A2 | 7/2003 |
| WO | 03095452 A1 | 11/2003 |
| WO | 03103972 A1 | 12/2003 |
| WO | WO 03/102134 A2 | 12/2003 |
| WO | 2004016747 A2 | 2/2004 |
| WO | WO 2004/011621 A2 | 2/2004 |
| WO | 2004044158 A2 | 5/2004 |
| WO | 2004050827 A2 | 6/2004 |
| WO | 2004055155 A2 | 7/2004 |
| WO | 2004073633 A1 | 9/2004 |
| WO | 2004087885 A2 | 10/2004 |
| WO | WO 2004/090110 A2 | 10/2004 |
| WO | WO2005001077 A2 | 1/2005 |
| WO | 2005017117 A2 | 2/2005 |
| WO | WO 2005/014799 A1 | 2/2005 |
| WO | 2005058301 A1 | 6/2005 |
| WO | 2005063971 A1 | 7/2005 |
| WO | WO 2005/065354 A2 | 7/2005 |
| WO | 2005080551 A2 | 9/2005 |
| WO | WO 2005/086845 A2 | 9/2005 |
| WO | WO 2005/116073 A2 | 12/2005 |
| WO | WO 2005/116073 A3 | 12/2005 |
| WO | 2006020919 A2 | 2/2006 |
| WO | WO 2006/016999 A | 2/2006 |
| WO | 2006026473 A1 | 3/2006 |
| WO | 2006100490 A1 | 9/2006 |
| WO | WO 2006/094286 A2 | 9/2006 |
| WO | 2006113470 A2 | 10/2006 |
| WO | 2006114098 A2 | 11/2006 |
| WO | 2006135824 A1 | 12/2006 |
| WO | 2006137787 A1 | 12/2006 |
| WO | 2006138433 A2 | 12/2006 |
| WO | 2007003525 A2 | 1/2007 |
| WO | 2007012144 A1 | 2/2007 |
| WO | 2007016485 A2 | 2/2007 |
| WO | WO 2007/030870 A1 | 3/2007 |
| WO | WO 2007027157 A1 | 3/2007 |
| WO | 2007047509 A1 | 4/2007 |
| WO | 2007051038 A2 | 5/2007 |
| WO | WO 2007/082963 A | 7/2007 |
| WO | WO 2007/103282 A | 9/2007 |
| WO | 2007127927 A2 | 11/2007 |
| WO | 2007149182 A2 | 12/2007 |
| WO | WO 2007/139929 | 12/2007 |
| WO | 2008004990 A2 | 1/2008 |
| WO | 2008013664 A1 | 1/2008 |
| WO | 2008035110 A1 | 3/2008 |
| WO | 2008036447 A2 | 3/2008 |
| WO | 2008048671 A1 | 4/2008 |
| WO | WO2008048647 A1 | 4/2008 |
| WO | 2008086005 A1 | 7/2008 |
| WO | 2008094597 A2 | 8/2008 |
| WO | 2008102118 A1 | 8/2008 |
| WO | 2009012428 A1 | 1/2009 |
| WO | 2009018453 A1 | 2/2009 |
| WO | 2009027644 A2 | 3/2009 |
| WO | 2009070592 A1 | 6/2009 |
| WO | 2009096902 A1 | 8/2009 |

(56) References Cited

FOREIGN PATENT DOCUMENTS

| WO | 2009101407 A2 | 8/2009 |
|---|---|---|
| WO | WO2009105570 A2 | 8/2009 |
| WO | 2009131568 A1 | 10/2009 |
| WO | 2010000415 A1 | 1/2010 |

OTHER PUBLICATIONS

Prowse et al. Proteomics, 5:978-989, 2005.*
Ellerstrom, Stem Cells, 24:2170-2176, Jun. 2006.*
Oh et al. Clin. and Exp. Pharmacology and Physiology, 33:489-495, 2006.*
Ludwig et al. Nat. Biotech., 24(2): 185-187, 2006.*
Xu et al. Nature Biotech.,19: 971-974, 2001.*
Amit et al. Dev. Biol., 227: 271-278, 2000.*
Amit et al. Biol. of Reprod., 70:837-845, 2004.*
Sidhu, Feb. 2006, Stem Cells and Development, 15:61-69.*
Invitrogen, Product News, TrypLETM Select and TrypLETM Express, 2004.*
Product Specification Sheet (Becton Dickinson, 2002, accessed by web at http://www.bdj.co.jp/pdf/35-SPC-356231.pdf on Jul. 26, 2010.*
TrypLE product description Life Technologies found at http://www.lifetechnologies.com/order/catalog/product/12563029 accessed online on Jan. 10, 2014.*
Ellerstrom, 2007, Stem Cells, 25:1690-1696.*
"Preserve the stability of yoru stem cells", Internet Citation, [online] 2006, retrieved from the Internet: URL:http//invitrogen.com.cn/etc/medialib/en/filelibrary/pdf.Par.96037.File.dat/F-066598%20TrypLE%20Flyer.pdf, retrieved on Sep. 13, 2008.
Braam, Stefan R. et al., "Improved genetic manipulation of human embryonic stem cells", Nature Methods, May 2008, vol. 5, No. 5, May 2008, pp. 389-392.
Denning, Chris et al., "Common culture conditions for maintenance and cardiomyocyte differentiation of the human embryonic stem cell lines, BG01 and HUES-7", International Journal of Developmental Biology, University of the Basque Country Pres, Leioa, ES, vol. 50, No. 1, Jan. 2006, pp. 27-37.
Ellestrom, C. et al., "Facilitated expansion of human embryonic stem cells by single-cell enzymaticdissociation", Stem Cells, Alphamed Press, Dayton, OH, vol. 25, No. 7, Mar. 2007, pp. 1690-1696.
Klimanskaya, Inina et al., "Human embryonic stem cells derived without feeder cells", Lancet (North American Edition), vol. 365, No. 9471, May 2005, pp. 1636-1641.
Panchision, David M. et al., "Optimized flow cytometric analysis of central nervous system tissue reveals novel functional relationships among cells expressing CD133, CD15, and CD24", Stem Cells, vol. 25, No. 6, Jun. 2007, pp. 1560-1570.
Wang, G. et al., "Noggin and bFGF cooperate to maintain pluripotency of human embryonic stem cells in the absence of feeder layers", Biochemical and Biophysical Research Communications, Academic Press, Inc., orlando, FL, vol. 330, No. 3, May 2005, pp. 934-942.
Xu, Chunhui et al., "Feeder-free growth of undifferentiated human embryonic stem cells", Nature Biotechnology, Nature Publishing Group, New York, NY, vol. 19, No. 10, Oct. 2001, pp. 971-974.
Amit et al (Biol. Reprod 68: 2150-2156, 2003).
Ausubel et al.Current Protocols in Molecular Biology, eds. 2001 supplement.
Benvenistry et al. (Benvenistry et al, Stem Cells 2006; 24:1923-1930).
Blyszczuk et al. (PNAS 100:998, 2003).
Cheon et al BioReprod 77 2007.
Ricordi et al Diabetes 37:413-420 (1988).
D'Amour et al, Nature Biotechnology 24, 1392-1401 (2006).
D'Amour et al, Nature Biotechnology 23, 1534-1541 (2005).
Gordon et al. (PNAS 103: 16806, 2006).
Harlow and Lane, Using Antibodies: A Laboratory Manual, New York: Cold Spring Harbor Laboratory Press (1998).
Hori et al. (PNAS 99: 16105, 2002).
Inzunza et al (Stem Cells 23: 544-549, 2005).
Lee, J.B. et al.: "Establishment and Maintenance of Human Embryonic Stem Cell Lines on Human Feeder Cells Derived from Uterine Endometricum under Serum-Free Condition" Biology of Reproduction, Society for the Study of Reproduction, Campaign, IL, US vol. 72, Jan. 1, 2005 pp. 42-49 XP008083585.
Levenstein et al (Stem Cells 24: 568-574, 2006).
McLean et al, Stem Cells 25, 29-38 (2007).
Micallef et al. (Diabetes 54:301, 2005).
Miyamoto et al (Stem Cells 22: 433-440, 2004).
Richards et al, (Stem Cells 21: 546-556, 2003).
Reubinoff et al (Nature Biotechnology 18: 399-404 (2000).
Shamblott et al., Proc. Natl. Acad. Sci. USA 95:13726, 1998.
Kubo et al, Development 131, 1651-1662 (2004).
Shiraki et al. Genes Cells. Jun. 2005; 10(6): 503-16.
Skoudy et al. (Biochem. J. 379: 749, 2004).
Stojkovic et al (Stem Cells 2005 23: 306-314, 2005).
Thompson et al (Science Nov. 6, 1998: vol. 282. No. 5391, pp. 1145-1147).
Wang et al (Stem Cells 23: 1221-1227, 2005).
Xu et al (Stem Cells 22: 972-980, 2004).
Gershengorn et al Science 306: 2261-2264, 2004.
Seaberg et al Nature Biotechnology 22: 1115-1124, 2004.
Bonner Wier et al Proc Nat Acad Sci 97: 7999-8004, 2000.
Curr. Top. Dev. Biol. 38:133 ff., 1998.
Thomson et al Proc. Natl. Acad. Sci. U.S.A. 92:7844, 1995.
Lumelsky et al. (Science 292:1389, 2001).
Soria et al. (Diabetes 49:157, 2000).
Miyazaki et al. (Diabetes 53: 1030, 2004).
Kleinman, H.K., et al., Biochemistry 25:312 (1986).
Hadley, M.A., et al., J.Cell.Biol. 101:1511 (1985).
Tulachan et al (Developmental Biology, 305, 2007, pp. 508-521).
Buzzard et al., "Karyotype of Human ES Cells During Extended Culture", Nature Biotechnology, 22(4) pp. 381-382 (2004).
Draper et al., "Recurrent Gain of Chromosomes 17q and 12 in Cultured Human Embryonic Stem Cells", Nature Biotechnology, 22(1) pp. 54-54 (2004).
Hasegawa et al., "A Method for the Selection of Human Embryonic Stem Cell Sublines with High Replating Efficiency After Single-Cell Dissociation", Stem Cells, 24, pp. 2649-2660 (2006).
Heng et al., "Mechanical Dissociation of Human Embryonic Stem Cell Colonies by Manual Scraping after Collagenase Treatment is Much More Detrimental to Cellular Viability than is Trypsinization with Gentle Pipetting", Biotechnology Applied Biochemistry, 47, pp. 33-37 (2007).
Mitalipova et al., "Preserving the Genetic Integrity of Human Embryonic Stem Cells", Nature Biotechnology, 23(1) (2005).
Nicholas et al., "A Method for Single-Cell Sorting and Expansion of Genetically Modified Human Embryonic Stem Cells", Stem Cells and Development, 16(1) pp. 109-118 (2007).
Abeyta, et al., Unique Gene Expression Signatures of Independently-Derived Human Embryonic Stem Cells Lines, Human Molecular Genetics, Jan. 28, 2004, pp. 601-608, vol. 13, No. 6, Oxford University Press.
Abranches, et al., Expansion of Mouse Embryonic Stem Cells on Microcarriers, Biotechnology Bioengineering, Apr. 15, 2007, pp. 1211-1221, vol. 96, No. 4, Wiley InterScience.
Ackermann, et al., Molecular Regulation of Pancreatic B-Cell Mass Development, Maintenance, and Expansion, Journal of Molecular Endocrinology, 2007, pp. 193-206, vol. 38.
Adams, J., Proteasome Inhibition in Cancer: Development of PS-341, Seminars in Oncology, 2001, pp. 613-619, vol. 28, No. 6.
Age-Related Eye Disease Study Research Group, A Randomized, Palcebo-Controlled, Clinical Trial of High-Dose Supplementation with Vitamins C and E, Beta Carotene, and Zinc for Age-Related Macular Degeneration and Vision Loss, Arch Ophthalmology, 2001, pp. 1417-1436, AREDS Report No. 8, vol. 119.
Allegrucci, et al., Differences between Human Embryonic Stem Cell Lines, Human Reproduction Update, Aug. 26, 2006, pp. 1-18, Advance Access.
Almond, et al., The Proteasome: A Novel Target for Cancer Chemotherapy, Leukemia, 2002, pp. 433-443, vol. 16.

(56) References Cited

OTHER PUBLICATIONS

Arai, et al., Purification of Recombinant Activin A Using the Second Follistatin Domain of Follistatin-Related Gene (FLRG), Protein Expression & Purification, 2006, pp. 78-82, vol. 49.

Armstrong, et al., The Role of P13K/AKT, MAPK/ERK and $NF_\kappa\beta$ Signalling in the Maintenance of Human Embryonic Stem Cell Pluripotency and Viability Highlighted by Transcriptional Profiling and Functional Analysis, Human Molecular Genetics, 2006, pp. 1894-1913, vol. 15, No. 11.

Baetge, Production of B-Cells from Human Embryonic Stem Cells, Diabetes, Obesity, Metabolism, 2008, pp. 186-194, vol. 10, Supplement 4.

Balsam, et al., Haematopoeitic Stem Cells Adopt Mature Haeatopoietic Fates in Ischaemic Myocardium, Nature, Apr. 8, 2004, pp. 668-673, Nature Publishing Group.

Barclay, et al., The Leucocyte Antigen Facts Book, The Leucocyte Antigen Facts Book, 1997, Textbook, 2[sup] edition, Academic Press.

Beltrami, et al., Adult Cardiac Stem Cells are Multipotent and Support Myocardial Regeneration, Cell, Sep. 19, 2003, pp. 763-776, vol. 114, Cell Press.

Bigdeli, et al., Adaptation of Human Embryonic Stem Cells to Feeder-Free and Matrix-Free Culture Conditions Directly on Plastic Surfaces, Journal of Biotechnology, 2008, pp. 146-153, vol. 133.

Blin, et al., A Purified Population of Multipotent Cardiovascular Progenitors Derived from Primate Pluripotent Stem Cells Engrafts in Postmyocardial Infarcted Nonhumans Primates, The Journal of Clinical Investigation, Apr. 2010, pp. 1125-1139, vol. 120, No. 4.

Bocian-Sobkowska, et al., Polyhormonal Aspect of the Endocrine Cells of the Human Fetal Pancreas, Histochem Cell Biol, 1999, pp. 147-153, vol. 112, Issue 2.

Borowiak, et al., How to Make AB Cells, Current Opinion Cell Biology, 2009, pp. 727-732, vol. 21, Issue 6.

Brakenhoff et al., Development of a Human Interleukin-6 Receptor Antagonist, Journal of Biological Chemistry, Jan. 7, 1994, 86-93, 269-1, US.

Brambrink, et al., Sequential Expression of Pluripotency Markers During Direct Reprogramming of Mouse Somatic Cells, Cell Stem Cell, 2008, pp. 151-159, vol. 2.

Brevig, et al., The Recognition of Adsorbed and Denatured Proteins of Different Topographies by β2 Integrins and Effects on Leukocyte Adhesion and Activation, Biomaterials, 2005, pp. 3039-3053, vol. 26.

Brevini, et al., No Shortcuts to Pig Embryonic Stem Cells, Theriogenology, 2010, pp. 544-550, vol. 74.

Bross, et al., Approval Summary for Bortezomib for Injection in the Treatment of Multiple Myeloma, Clinical Cancer Research, Jun. 15, 2004, pp. 3954-3964, vol. 10.

Brown, et al., Optimal Control of Blood Glucose: The Diabetic Patient or the Machine?, Science Translation Medicine, Apr. 14, 2010, pp. 1-5, vol. 2 Issue 27.

Burkard et al, Conditional Neuronal Nitric Oxide Synthase Overexpression Impairs Myocardial Contractility, Circulation Reseach, Jan. 18, 2007, pp. e32-e44, vol. 100.

Cai, et al., Generation of Homogeneous PDX1+Pancreatic Progenitors from Human ES Cell-derived Endoderm Cells, Journal of Molecular Cell Biology, Nov. 12, 2009, pp. 50-60, vol. 2.

Castaing, et al., Blood Glucose Normalization Upon Transplantation of Human Embryonic Pancreas into Beta-Cell-Deficient SCID Mice, Diabetologica, 2001, pp. 2066-2076, vol. 44.

Chambers, et al., Functional Expression Cloning of Nanog, a Pluripotency Sustaining Factor in Embryonic Stem Cells, Cell, May 30, 2003, pp. 643-655, vol. 113.

Chapple, et al., Unfolding Retinal Dystrophies: A Role for Molecular Chaperones?, Trends in Molecluar Medicine, 2001, pp. 414-421, vol. 7, No. 9.

Chen, et al., A Small Molecule that Directs Differentiation of Human ESCs into the Pancreatic Lineage, Nature Chemical Biology, Apr. 11, 2009, pp. 258-265, vol. 5, No. 4.

Chen, et al., Chemically Defined Conditions for Human iPSC Derivation and Culture, Nature Methods, 2011, pp. 424-429, vol. 8, Issue 5.

Chen, et al., Differentiation of Rat Marrow Mesencymal Stem Cells in Pancreatic Islet Beta-Cells, World Journal of Gastroenterology, Oct. 15, 2004, pp. 3016-3020.

Cheon, et al., Defined Feeder-Free Culture System of Human Embryonic Stem Cells, Biol Reprod, 2005, 105.046870, DOI10/1095.

Chung, et al., Human Embryonic Stem Cell Lines Generated without Embryo Destruction, Cell Stem Cell, 2008, pp. 113-117, vol. 2.

Corbeil, et al., Rat Prominin, Like its Mouse and Human Orthologues, is a Pentaspan Membrane Glycoprotein, Biochemical and Biophysical Research Communications, 2001, pp. 939-944, vol. 285, No. 4.

Crane, et al., An Embryogenic Model to Explain Cytogenetic Inconsistencies Observed in Chorionic Villus Versus Fetal Tissue, Prenatal Diagnosis, 1988, pp. 119-129, vol. 8.

Cresta, et al., Phase I Study of Bortezomib with Weekly Paclitaxel in Patients with Advanced Solid Tumours, European Journal of Cancer, 2008, pp. 1829-1834, vol. 44.

Cure, et al., Improved Metabolic Control and Quality of Life in Seven Patients with Type 1 Diabetes Following Islet After Kidney Transplantation, Cell Therapy and Islet Transplantation, Mar. 27, 2008, pp. 801-812, vol. 85, No. 6.

David M. Chacko, et al., Survival and Differentiation of Cultured Retinal Progenitors Transplanted in the Subretinal Space of the Rat, Biochemical and Biophysical Research Communications, 2000, pp. 842-846, vol. 268, Academic Press.

De Coppi, et al., Isolation of Amniotic Stem Cell Lines with Potential for Therapy, Nature Biotechnology, 2007, pp. 100-106, vol. 25, No. 1.

Donovan, et al., The End of the Beginning for Pluripotent Stem Cells, Nature, Nov. 2001, pp. 92-97, vol. 414.

Dorrell, et al., Editorial, Stem Cell Research, 2008, pp. 155-156, vol. 1.

Doyle, et al., Cell and Tissue Culture: Laboratory Procedures in Biotechnology, Cell and Tiossue Culture: Laboratory Procedures in Biotechnology, 1995, Textbook, Textbook, Wiley.

Draper, et al., Surface Antigens of Human Embryonic Stem Cells: Changes Upon Differentiation in Culture, Journal Anatomy, 2002, pp. 249-258, vol. 200, Anatomical Society of Great Britain and Ireland.

Dupont-Gillain, et al., Plasma-Oxidized Polystyrene: Wetting Properties and Surface Reconstruction, Langmuir, 2000, pp. 8194-8200, vol. 16.

Edlund, Pancreatic Organogenisis—Pancreatic Mechanisims and Implications for Therapy, Nature, Jul. 1, 2002, 524-532, 3, Nature Publishing Group, US.

Ellmers, et al., Transforming Growth Factor-B Blockade Down-Regulates the Renin-Angiotensin System and Modifies Cardiac Remodling after Myoardial Infarction, Endocrinology, Jul. 24, 2008, pp. 5828-5834, vol. 149—Issue 11, The Endocrine Society.

Enzmann, et al., Enhanced Induction of RPE Lineage Markers in Pluripootent Neural Stem Cells Engrafted into the Adult Rat Subretinal Space, Investigative Ophthamology & Visual Science, Dec. 2003, pp. 5417-5422, vol. 44, No. 12, Association for Research in Vision and Ophthamology.

Eventov-Friedman, et al., Embryonic Pig Pancreatic Tissue Transplantation for the Treatment of Diabetes, PLoS Medicine, Jul. 2006, e215, pp. 1165-1177, vol. 3, Issue 7.

Ezashi, et al., Low 02 Tensions and the Prevention of Differentiation of hES Cells, Proceedings of the National Academy of Sciences of USA, Mar. 29, 2005, pp. 4783-4788, vol. 102, No. 13.

Fauza, Amniotic Fluid and Placental Stem Cells, Ballieres Best Practice and Research Clinical Obsterics and Gynaecology, 2004, pp. 877-891, vol. 18, No. 6.

Fidler et al., Selective Immunomodulation by the Antineoplastic Agent Mitoxantrone, Journal of Immunology, Jul. 15, 1986, 727-732, 137-2, American Society of Immunologists, US.

Fischer, et al., Residues in the C-Terminal Region of Activin A Determine Specificity for Follistatin and Type II Receptor Binding, Journal of Endocrinology, 2003, pp. 61-68, vol. 176, Society for Endocrinology.

(56) References Cited

OTHER PUBLICATIONS

Fok, et al., Shear-Controlled Single-Step Mouse Embryonic Stem Cell Expansion and Embryoid Body-Based Differentiation, Stem Cells, 2005, pp. 1333-1342, vol. 23.

Frandsen et al., Activin B mediated induction of Pdx1 in human embryonic stemcell derived embryoid bodies, Biochemical and Biophysical Research Communications, Aug. 15, 2007, 568-574, 362, Elsevier Inc.

Fung, et al., The Effect of Medical Therapy and Islet Cell Transplantation on Diabetic Nephropathy: An Interim Report, Transplantation, Jul. 15, 2007, pp. 17-22, vol. 84, No. 1.

Gaspar, et al., Inhibition of Transforming Growth Factor Signaling Reduces Pancreatic Adenocarcinoma Growth and Invasiveness, Molecular Pharmacology, 2007, pp. 152-161, vol. 72, Issue 1.

Giltaire, et al., The CYP26 Inhibitor R115866 Potentiates the Effects of All-Trans Retinoic Acid on Cultured Human Epidermal Keratinocytes, British Journal of Dermatology, 2009, pp. 505-513, vol. 160.

Ginis, et al., Differences Between Human and Mouse Embryonic Stem Cells, Developmental Biology, 2004, pp. 360-380, vol. 269.

Gosden, et al., Amniotic Fluid Cell Types and Culture, British Medical Bulletin, 1983, pp. 348-354, vol. 39, No. 4.

Graham, et al., Characteristics of a Human Cell Line Transformed by DNA from Human Adenovirus Type 5, Journal General Virology, 1977, pp. 59-72, vol. 36.

Guo, et al., Stem Cells to Pancreatic B-Cells: New Sources for Diabetes Cell Therapy, Endocrine Reviews, May 2009, pp. 214-227, vol. 30, No. 3, The Endocrine Society.

Hamann, et al., Phenotypic and Functional Separation of Memory and and Effector Human CD8+ T Cells, Journal of Experimental Medicine, Mar. 11, 1997, 1407-1418, 186-9, Rockefeller University Press, US.

Harb, et al., The Rho-Rock-Myosin Signaling Axis Determines Cell-Cell Integrity of Self-Renewing Pluripotent Stem Cells, Plos One, 2008, Article e3001, XP002530386, vol. 3, Issue 8.

Haruta, et al., In Vitro and In Vivo Characterization of Pigment Epithelieal Cells Differentiated from Primate Embryonic Stem Cells, Investigative Ophthalmology & Visual Science, Mar. 2004, pp. 1020-1025, vol. 45, No. 3, Association for Research in Vision and Ophthalmology.

Hashemi, et al., A Placebo Controlled, Dose-Ranging, Safety Study of Allogenic Mesenchymal Stem Cells Injected by Endomyocardial Delivery after an Acute Myocardial Infarction, European Heart Journal, Dec. 11, 2007, pp. 251-259, vol. 29.

Held, et al., The Effect of Oxygen Tension on Colony Formation and Cell Proliferation of Amniotic Fluid Cells In-Vitro, Prenatal Diagnosis, 1984, pp. 171-180, vol. 4, No. 3.

Henderson, et al., Preimplantation Human Embryos and Embryonic Stem Cells Show Comparable Expression of Stage-Specific Embryonic Antigens, Stem Cells, 2002, pp. 329-337, vol. 20.

Herzenberg, et al., Fluorescence-activated Cell Sorting, Scientific American, 1976, 108-117, 234, Scientific American, US.

Hess, et al., Bone Marrow-Derived Stem Cells Initiate Pancreatic Regeneration, Nature Biotechnology, Jul. 2003, pp. 763-770, vol. 21, No. 7.

Hichem Frigui, et al., A Robust Competitive Clustering Algorithm With Applications in Computer Vision, IEEE, May 1, 1999, 450-465, 21-5, IEEE, US.

Ho, et al., Animal Cell Bioreactors, Animal Cell Bioreactors, 1991, 1-512, Hardcover, Butterworth-Heinemann.

Hoehn, et al., Morphological and Biochemical Heterogeneity of Amniotic Fluid Cells in Culture, Methods in Cell Biology, 1982, pp. 11-34, vol. 26, Academic Press, Inc.

Hussain, et al., Stem-Cell Therapy for Diabetes Mellitus, Lancet, 2004, pp. 203-205, vol. 364.

Ianus, et al., In Vivo Derivation of Glucose-Competent Pancreatic Endocrine Cells from Bone Marrow Without Evidence of Cell Fusion, The Journal of Clinical Investigation, Mar. 2003, pp. 843-850, vol. 111, No. 6.

Inami, et al., Differentiation of Induced Pluripotent Stem Cells to Thymic Epithelial Cells by Phenotype, Immunology and Cell Biology, Jun. 24, 2010, pp. 1-8, doi:10.1038/icb.2010.96.

Int' Anker, et al., Amniotic Fluid as a Novel Source of Mesenchymal Stem Cells for Therapeutic Transplantation, Blood, Aug. 15, 2003, pp. 1548-1549, vol. 102, No. 4.

Jafary, et al., Differential effect of activin on mouse embryonic stem cell differentiation in insulin-secreting cells under nestin-positive selection and spontaneous differentiation protocols, Cell Biology International, 2008, 278-286, 32, Elsevier.

Jeon, et al., Endocrine Cell Clustering During Human Pancreas Development, J Histochem Cytochem, 2009, pp. 811-824, vol. 57, Issue 9.

Jiang, et al., Generation of Insulin-Producing Islet-Like Clusters from Human Embryonic Stem Cells, Stem Cells, 2007, pp. 1940-1953, vol. 25, Issue 8.

Johansson, et al., Temporal Control of Neurogenin3 Activity in Pancreas Progenitors Reveals Competence Windows for the Generation of Different Endocrine Cell Types, Developmental Cell, Mar. 2007, pp. 457-465, vol. 12.

Kahan, Pancreatic Precursors and Differentiated Islet Cell Types from Murine Embryonic Stem Cells, Diabetes, Aug. 2003, pp. 2016-2042, vol. 52.

Kelly, et al., Cell-Surface Markers for the Isolation of Pancreatic Cell Types Derived from Human Embryonic Stem Cells, Nature Biotechnology, 2011, pp. 750-756, vol. 29, Issue 8.

Kicic, et al., Differentiation of Marrow Stromal Cells into Photoreceptors in the Rat Eye, The Journal of Neuroscience, Aug. 27, 2003, pp. 7742-7749, vol. 23, Issue 21.

Kingsley, The TGF-B Superfamily: New Members, New Receptors, and New Genetic Tests of Function in Different Organisms, Genes & Development, 1994, pp. 133-146, XP009011502, vol. 8, Cold Spring Harbor Laboratory Press.

Kinkel, et al., Cyp26 Enzymes Function in Endoderm to Regulate Pancreatic Field Size, PNAS, May 12, 2009, pp. 7864-7869, vol. 106, No. 19.

Koblas, et al., Differentiation of CD133-Positive Pancreatic Cells Into Insulin-Producing Islet-Like Cell Clusters, Transplantation Proceedings, 2008, pp. 415-418, vol. 40.

Kohen, et al., Characterization of Matrigel Interfaces During Defined Human Embryonic Stem Cell Culture, Biointerphases, Dec. 2009, pp. 6979.

Koller, et al., Effects of Synergistic Cytokine Combinations, Low Oxygen, and Irradiated Stroma on the Expansion of Human Cord Blood Progenitors, Blood, Jul. 15, 1992, pp. 403-411, vol. 80, No. 2.

Koyangi et al., Inhibitio nof the Rho/ROCK Pathway Reduces Apoptosis During Transplantatation of Embryonic Stem Cell-Derived Neural Precursors, Journal of Neurosciene Research, Sep. 7, 2007, 270-280, 86, Wiley-Liss, Inc.

Krapcho et al., Synthesis and Antineoplastic Evaluations of 5,8-Bis[(aminoalkyl)amino]-1-azaanthracene-9,10-diones, Journal of Medical Chemistry, 1985, 1124-1126, 28, American Chemical Society.

Krawetz, et al., Human Embryonic Stem Cells: Caught Between a ROCK Inhibitor and a Hard Place, BioEssays: News and Reviews in Molecular Cellular and Developmental Biology, 2009, pp. 336-343, vol. 31.

Kron, et al., Expression of Human Activin C Protein in Insect Larvae Infected with a Recombinant Baculovirus, Journal of Virological Methods, 1998, pp. 9-14, vol. 72.

Kroon, et al., Pancreatic Endoderm Derived from Human Embryonic Stem Cells Generates Glucose-Responsive Insulin-Secreting Cells in vivo, Nature Biotechnology, Apr. 2008, pp. 443-452, vol. 26, No. 4.

Ku et al., Committing Embryonic Stem Cells to Early Endocrine Pancreas In Vitro, Stem Cells, 2004, 1205-1217, 22, AlphaMed Press.

Lanza, et al., Characteristics and Characterization of Human Pluripotent Stem Cells, Stem Cell Anthology, 2010, pp. 141, 142, 144 and 146, 1st Edition.

Laplante, et al., RhoA/ROCK and Cdc42 Regulate Cell-Cell Contact and N-Cadherin Protein Level During Neurodetermination of P19 Embryonal Stem Cells, Journal of Neurobiology, 2004, pp. 289-307, vol. 60, No. 3.

(56) References Cited

OTHER PUBLICATIONS

Larsen, et al., Evaluation of B-Cell Mass and Function in the Gottingen Minipig, Diabetes, Obesity and Metabolism, 2007, pp. 170-179, vol. 9, Supplement 2, Blackwell Publishing Ltd.

Le Blanc, et al., Mesenchymal Stem Cells Inhibit and Stimulate Mixed Lymphocyte Cultures and Mitogenic Responses Independently of the Major Histocompatibility Complex, Scandinavian Journal of Immunology, 2003, pp. 11-20, vol. 57, Blackwell Publishing Ltd.

Lee, et al., Human B-cell Precursors Mature into Functional Insulin-Producing Cells in an Immunoisolation Device: Implications for Diabetes Cell Thereapies, Transplantation, Apr. 15, 2009, pp. 983-991, vol. 87, No. 7.

Lee, et al., Retionic Acid-Induced Human Secretin Gene Expression in Neuronal Cells is Mediated by Cyclin-Dependent Kinase 1, Annals of the New York Academy of Sciences, 2006, pp. 393-398, vol. 1070.

Li, et al., Generation of Rat and Human Induced Pluripotent Stem Cells by Combining Genetic Reprogramming and Chemical Inhibitors, Cell Stem Cell, Jan. 9, 2009, pp. 16-19, vol. 4.

Lilja et al., Cyclin-dependent Kinase 5 Promotes Insulin Exocytosis, Journal of Biological Chemistry, Jul. 6, 2001, 34199-34205, 36-7, JBC Papers in Press.

Liu, et al., A Novel Chemical-Defined Medium with bFGF and N2B27 Supplements Supports Undifferentiated Growth in Human Embryonic Stem Cells, Biochemical and Biophysical Research Communications, 2006, pp. 131-139, vol. 346.

Loh, et al., Genomic Approaches to Deconstruct Puripotency, Annu Rev Genomics Hum Genet, 2011, pp. 165-185, vol. 12.

Lund, et al., Cell Transplantation as a Treatment for Retinal Disease, Progress in Retinal and Eye Research, 2001, pp. 415-449, vol. 20, No. 4, Elsevier Science Ltd.

Lund, et al., Retinal Transplantation: Progress and Problems in Clinical Application, Journal of Leukocyte Biology, Aug. 2003, pp. 151-160, vol. 74.

Lyttle, et al., Transcription Factor Expression in the Developing Human Fetal Endocrine Pancreas, Diabetologica, 2008, pp. 1169-1180, vol. 51, Spring-Verlag.

MacFarlane, et al., Glucose Stimulates Translocation of the Homeodomain Transcription Factor PDX1 from the Cytoplasm to the Nucleus in Pancreatic B-Cells, The Journal of Biological Chemistry, 1999, pp. 1011-1016, vol. 274, No. 2.

Maherali, et al., Directly Reprogrammed Fibroblasts Show Global Epigenetic Remodeling and Widespread Tissue Contribution, Cell Stem Cell, Jul. 2007, pp. 55-70, vol. 1, Elsevier, Inc.

Marshall, et al., Early Micro-and Macro-Angiopathy in the Streptozotocin, Research in Experimental Medicine, 1980, pp. 145-158, vol. 177, Springer-Verlag.

Marshall, et al., Isolation and Maintenance of Primate Embryonic Stem Cells, Methods in Molecular Biology, 2001, pp. 11-18, vol. 158.

Martin, et al., Bioreactors for Tissue Mass Culture: Design, Characterization, and Recent Advances, Biomaterials, Jul. 14, 2005, pp. 7481-7503, vol. 26.

Marzo, et al., Pancreatic Islets from Cyclin-Dependent Kinase 4/R24C (Cdk4) Knockin Mice have Significantly Increased Beta Cell Mass and are Physiologically Functional, Indicating that Cdk4 is a Potential Target for Pancreatic . . . , Diabetologia, 2004, pp. 686-694, vol. 47.

McKiernan, et al., Directed Differentiation of Mouse Embryonic Stem Cells into Pancreatic-Like or Neuronal-and Glial-Like Phenotypes, Tissue Engineering, 2007, pp. 2419-2430, vol. 13, No. 10.

McLin, et al., Repression of WNT/(szligbeta)-6atenin Signaling in the Anterior Endoderm is Essential for Liver and Pancreas Development, Development, 2007, pp. 2207-2217, vol. 134, Issue 12.

Meijer, et al., Pharmacological Inhibitors of Glycogen Synthase Kinase 3, Trends in Pharmacological Sciences, Sep. 2004, pp. 471-480, vol. 25, No. 9.

Michael J. Borowitz, et al., Prognostic Significance of Fluorescence Intensity of Surface Marker . . . , Blood, Jun. 1, 1997, 3960-3966, 89-11, American Society of Hematology, Washington, D.C., US.

Miller, et al., The Pig as a Model for Human Nutrition, Annual Review of Nutrition, 1987, pp. 361-382, vol. 7, Annual Reviews Inc.

Milunsky, et al., Genetic Disorders and the Fetus: Diagnosis Prevention and Treatment, Pediatric and Developmental Pathology, 2011, pp. 84, vol. 14, Society for Pediatric Pathology.

Mitsui, et al., The Homeoprotein Nanog is Required for Maintenance of Pluripotency in Mouse Epiblast and ES Cells, Cell, May 30, 2003, pp. 631-642, vol. 113, Cell Press.

Moore, et al., The Corneal Epithelial Stem Cell, DNA and Cell Biology, 2002, pp. 443-451, vol. 21, No. 5/6.

Moran, et al., Bidirectional-Barbed Sutured Knotless Running Anastomosis v Classic van Velthoven in a Model System, Journal of Endourology, 2007, pp. 1175-1177, vol. 21, No. 10.

Morrison, et al., Culture in Reduced Levels of Oxygen Promotes Clonogenic Sympathoadrenal Differentiation by Isolated Neural Crest Stem Cells, Journal of Neuroscience, Oct. 1, 2000, pp. 7370-7376, vol. 20, No. 19.

Movassat, et al., Keratinocyte Growth Factor and Beta-Cell Differentiation in Human Fetal Pancreatic Endocrine Precursor Cells, Diabetologia, 2003, pp. 822-829, vol. 46.

Muchamuel, et al., Preclinical Pharmacology and in Vitro Characterization of PR-047, An Oral Inhibitor of the 20s Proteasome, Blood, Nov. 16, 2008, p. 1257, vol. 112, No. 11.

Munoz, et al., Conventional Pluripotency Markers are Unspecific for Bovine Embryonic-Derived Cell-Lines, Theriogenology, 2008, pp. 1159-1164, vol. 69.

Murtha, et al., Evaluation of a Novel Technique for Wound Closure Using a Barbed Suture, Cosmetic, Aug. 2, 2005, pp. 1769-1780, vol. 117, No. 6.

Nakagawa, et al., Generation of Induced Pluripotent Stem Cells without Myc from Mouse and Human Fibroblasts, Jan. 2008, pp. 101-106, vol. 26, No. 1.

Nakamura, et al., Ocular Surface Reconstruction Using Cultivated Mucosal Epithelial Stem Cells, Cornea, Oct. 2003, S75-S80, vol. 22, Supplement 1.

Nishimura, et al., Expression of MafA in Pancreatic Progenitors is Detrimental for Pancreatic Development, Developmental Biology, 2009, pp. 108-120, vol. 333.

Nostro, et al., Stage-Specific Signaling Through TGF Family Members and WNT Regulates Patterning and Pancreatic Specification of Human Pluripotent Stem Cells, Development, 2011, pp. 861-871, vol. 138, Issue 5.

Okita, et al., Generation of Germline-Competent Induced Pluripotent Stem Cells, Nature, Jul. 19, 2007, pp. 313-317, vol. 448.

Orlowski, et al., Safety and Antitumor Efficacy of the Proteasome Inhibitor Carfilzomib (PR-171) Dosed for Five Consecutive Days in Hematologic Malignancies: Phase 1 Results, Blood, 2007, Part 1, vol. 110, No. 11.

Osborne, et al., Some Current Ideas on the Pathogenesis and the Role of Neuroprotection in Glaucomatous Optic Neuropathy, European Journal of Ophthalmology, 2003, S19-S26, vol. 13, Supplement 3, Wichtig Editore.

Ostrom, et al., Retinoic Acid Promotes the Generation of Pancreatic Endocrine Progenitor Cells and Their Further Differentiation into B-Cells, PLOS One, Jul. 30, 2008, e2841, pp. 1-7, vol. 3, No. 7.

Paling, et al., Regulation of Embryonic Stem Cell, Self-Renewal by Phosphoinositide 3-kinase-dependent Signaling, Journal of Biological Chemistry, 2004, pp. 48063-48070, vol. 279, No. 46.

Panepinto, et al., The Yucatan Miniature Pig: Characterization and Utilization in Biomedical Research, Laboratory Animal Science, Aug. 1986, pp. 344-347, vol. 36, No. 4, American Association for Laboratory Animal Science.

Pangas, et al., Production and Purification of Recombinant Human Inhibin and Activin, Journal of Endocrinology, 2002, pp. 199-210, vol. 172.

Pardo, et al., Corning CellBIND Surface: An Improved Surface for Enhanced Cell Attachment, Corning Technical Report, 2005, 8 page report, XP002530385.

Paris, et al., Equine Embryos and Embryonic Stem Cells: Defining Reliable Markers of Pluripotency, Theriogeneology, 2010, pp. 516-524, vol. 74.

(56) References Cited

OTHER PUBLICATIONS

Peerani, et al., Niche-Mediated Control of Human Embryonic Stem Cell Self-Renewal and Differentiation, The EMBO Journal, 2007, pp. 4744-4755, vol. 26.
Peter O. Krutzik, et al., Coordinate Analysis of Murine Immune Cell Surface Markers and Intracellular Phosphoproteins by Flow Cytometry, Journal of Immunology, May 30, 2005, 2357-2365, 175, American Association of Immunologists, Inc., US.
Phillips, et al., Attachment and Growth of Human Embryonic Stem Cells on Microcarriers, Journal of Biotechnology, 2008, pp. 24-32, vol. 138.
Pouton, et al., Embryonic Stem Cells as a Source of Models for Drug Discovery, Nature Reviews Drug Discovery, Aug. 2007, pp. 1474-1776, vol. 6, No. 8.
Prichard, et al., Adult Adipose Derived Stem Cell Attachment to Biomaterials, Biomaterials, 2006, pp. 936-946, vol. 28, No. 6.
Prusa, et al., Oct. 4-Expressing Cells in Human Amniotic Fluid: a New Source for Stem Cell Research?, Human Reproduction, 2003, pp. 1489-1493, vol. 18, No. 7.
Rajagopal, et al., Insulin Staining of ES Cell Progeny from Insulin Uptake, Science, Jan. 17, 2003, pp. 363, vol. 299.
Rao, Conserved and Divergent Paths that Regulate Self-Renewal in Mouse and Human Embryonic Stem Cells, Developmental Biology, Aug. 10, 2004, pp. 269-286, vol. 275, Elsevier, Inc.
Rebbapragada, et al., Myostatin Signals Through a Transforming Growth Factor B-Like Signaling Pathway to Block Adipogenesis, Molecular and Cellular Biology, 2003, pp. 7230-7242, vol. 23, No. 20.
Rebollar, et al., Proliferation of Aligned Mammalian Cells on Laser-Nanostructured Polystyrene, Biomaterials, 2008, pp. 1796-1806, vol. 29.
Reisner, Growing Organs for Transplantation form Embryonic Precursor Tissues, Immunol. Res., 2007, pp. 261-273, vol. 38.
Rezania, Production of Functional Glucagon-Secreting-Cells from Human Embryonic Stem Cells, Diabetes, 2011, pp. 239-247, vol. 60, Issue 1.
Richardson, et al., Bortezomid (PS-341): A Novel, First-in-Class Proteasome Inhibitor for the Treatement of Multiple Myeloma and Other Cancers, Cancer Control, 2003, pp. 361-369, vol. 10, No. 5.
Ryan, et al., Clinical Outcomes and Insulin Secretion After Islet Transplantation with the Edmonton Protocol, Diabetes, Apr. 2001, pp. 710-719, vol. 50.
Sakaguchi, et al., Integration of Adultmesenchymal Stem Cells in the CNS, Society for Neuroscience Abstract Viewer and Itineray Planner, 2002, XP002519394, Program 237.18.
Sato et al., Maintenance of Pluripotency in Human and Mouse Embryonic Stem Cells Through Activation of Wnt Signaling by a Pharmacological GSK-3-specific Inhibitor, Nature Medicine, Jan. 2004, pp. 55-63, vol. 10, No. 1.
Sato, et al., Manipulation of Self-Renewal in Human Embryonic Stem Cells Through a Novel Pharmacological GSK-3 Inhibitor, Methods in Molecular Biology, 2006, pp. 115-128, vol. 331.
Sato, et al., Molecular Signature of Human Embryonic Stem Cells and its Comparison with the Mouse, Developmental Biology, Apr. 23, 2003, pp. 404-413, vol. 260.
Savino et al., Generation of Interleukin-6 Receptor Antagonists by Molecular-Modeling Guided Mutagenesis of Residues Important for gp130 Activation, EMBO Journal, 1994, 1357-1367, 13-6, IT.
Schraermeyer, et al., Subretinally Transplanted Embryonic Stem Cells Rescue Photoreceptor Cells From Degeneration in the RCS Rats, Cell Transplantation, 2001, pp. 673-680, vol. 10.
Schroeder, et al., Differentiation of Mouse Embryonic Stem Cells to Insulin-Producing Cells, Nature Protocols, 2005, pp. 495-507, vol. 1, No. 2.
Scullica, et al., Diagnosis and Classification of Macular Degenerations: an Approach Based on Retinal Function Testing, Documenta Ophthalmologica, 2001, pp. 237-250, vol. 102.
Segev, et al., Differentiation of Human Embryonic Stem Cells into Insulin-Producing Clusters, Stem Cells, Jan. 1, 2004, pp. 265-274.
Shackleton, et al., Generation of a Functional Mammary Gland from a Single Stem Cell, Nature, Jan. 5, 2006, pp. 84-88, XP002567665, vol. 439.
Shapiro, et al., Islet Transplantation in Seven Patients with Type 1 Diabetes Mellitus Using a Glucocorticoid-Free Immunosuppressive Regimen, The New England Journal of Medicine, Jul. 27, 2000, pp. 230-238, vol. 343, No. 4, The Massachusetts Medical Society.
Shen, et al., The Effects of Surface Chemistry and Adsorbed Proteins on Monocyte/Macrophage Adhesion to Chemically Modified Polystyrene Surfaces, Journal of Biomedical Matter Research, 2001, pp. 336-345, vol. 57.
Sherwood, et al., Transcriptional Dynamics of Endodermal Organ Formation, Developmental Dynamics, 2009, pp. 29-42, vol. 238, Issue 1.
Shi et al., Inducing Embryonic Stem Cells to Differentiate into Pancreatic β Cells by a Novel Three-Step Approach with Activin A and All-Trans Retinoic Acid, Stem Cells, 2005, 656-662, 23, AlphaMed Press.
Schindler et al., A synthetic nanofibrillar matrix promotes in vivo-like organization and morphogenesis for cells in culture, Biomaterials, Apr. 18, 2005, 5624-5631, 26, Elsevier.
Shiraki, et al., Guided Differentiation of Embryonic Stem Cells into Pdx1-Expressing Regional-Specific Definitive Endoderm, Stem Cells, 2008, pp. 874-885, vol. 26.
Simons, et al., Assembly of Protein Tertiary Structures from Fragments with Similar Local Sequences Using Simulated Annealing and Bayesian Scoring Functions, Journal of Molecular Biology, 1997, pp. 209-225, vol. 268.
Simons, et al., Improved Recognition of Native-Like Protein Structures Using a Combination of Sequence-Dependent and Sequence-Independent Features of Proteins, Proteins: Structure, Function, and Genetics, 1999, pp. 82-95, vol. 34, Wiley-Liss, Inc.
Smith et al., Anti-Interleukin-6 Monoclnal Antibody Induces Regression of Human Prostate Cancer Xenografts in Nude Mice, The Prostate, Mar. 2, 2001, 47-53, 48, Wiley-Liss, Inc.
Stadtfeld, et al., Defining Molecular Cornerstones During Fibroblast to iPS Cell Reprogramming in Mouse, Cell Stem Cell, Mar. 2008, pp. 230-240, vol. 2.
Stafford, et al., Retinoic Acid Signaling is Required for a Critical Early Step in Zebrafish Pancreatic Development, Current Biology, 2002, pp. 1215-1220, vol. 12, Issue 14.
Stephen D. De Rosa, 11-color, 13-parameter flow cytometry: Identification of . . . , Nature, Feb. 1, 2001, 245-248, 7-2, Nature Publishing Group, US.
Sugiyama, et al., Conserved Markers of Fetal Pancreatic Epithelium Permit Prospective Isolation of Islet Progenitor Cells by FACS, PNAS, Jan. 2, 2007, pp. 175-180, vol. 104, No. 1.
Sugiyama, et al., Fluorescence-Activated Cell Sorting Purification of Pancreatic Progenitor Cells, Diabetes, Obesity and Metabolism, 2008, pp. 179-185, vol. 10, Supplement 4.
Suh, et al., Characterization of His-X3-His Sites in a-Helices of Synthetic Metal-Binding Bovine Somatotropin, Protein Engineering, 1991, pp. 301-305, vol. 4, No. 3.
Sulzbacher, et al., Activin A-Induced Differentiation of Embryonic Stem Cells into Endoderm and Pancreatic Progenitors—The Influence of Differentiation Factors and Culture Conditions, Stem Cell Rev, 2009, pp. 159-173, vol. 5.
Takahashi, et al., Homogenous Seeding of Mesenchymal Stem Cells into Nonwoven Fabric for Tissue Engineering, Tissue Engineering, 2003, pp. 931-938, vol. 9, No. 5.
Takahashi, et al., Induction of Pluripotent Stem Cells from Adult Human Fibroblasts by Defined Factors, Cell, 2007, pp. 861-872, vol. 131.
Takehara, et al., Rho-Associate Kinase Inhibitor Y-27632 Promotes Survival of Cynomolgus Monkey Embryonic Stem Cells, Molecular Human Reproduction, 2008, pp. 627-634, vol. 14, No. 11.
Tang, et al., Reprogramming Liver-Stem WB Cells into Functional Insulin-Producing Cells by Persistent Expression of Pdx1-and Pdx1-VP16 Mediated by Lentiviral Vectors, Laboratory Investigation, 2006, pp. 83-93, vol. 86.

(56) References Cited

OTHER PUBLICATIONS

Tannock, et al., Chemotherapy with Mitoxantrone Plus Prednisone or Prednisone Alone for Symptomatic Hormone-Resistant Prostate Cancer: A Canadian Randomized Trial With Palliative End Points, Journal of Clinical Oncology, 1996, 1756-1764, 14-6, American Society of Clinical Oncology, US.
Teare, et al., Cellular Attachment to Ultraviolet Ozone Modified Polystyrene Surfaces, Langmuir, 2000, pp. 2818-2824, vol. 16.
Tomita, et al., Bone Marrow-Derived Stem Cells Can Differentiate into Retinal Cells in Injured Rat Retina, Stem Cells, 2002, pp. 279-283, vol. 20.
Tsai, et al., Isolation of Human Multipotent Mesenchymal Stem Cells from Second-Trimester Amniotic Fluid Using a Novel Two-Stage Culture Protocol, Human Reproduction, Apr. 22, 2004, pp. 1450-1456, vol. 19, No. 6.
Ubeda et al., Inhibition of Cyclin-dependent Kinase 5 Activity Protects Pancreatic Beta Cells from Glucotoxicity, Journal of Biological Chemistry, Aug. 3, 2006, 28858-28864, 39, JBC Papers in Press.
Uludag, et al., Technology of Mammalian Cell Encapsulation, Advanced Drug Delivery Reviews, 2000, pp. 29-64, vol. 42.
Ungrin, et al., Reproducible, Ultra High-Throughput Formation of Multicellular Organization from Single Cell Suspension-Derived Human Embryonic Stem Cell Aggregates, Plos ONE, 2008, e1565, pp. 1-12, vol. 3, Issue 2.
Unknown, MeSH Descriptor Data, National Library of Medicine—Medical Subject Headings, Feb. 26, 1992, XP002553615.
Vacanti, et al., Selective Cell Transplantation Using Bioabsorbable Artificial Polymers as Matrices, Journal of Pediactric Surgery, Jan. 1988, 3-9, 23-1.
Valet, et al., Pretherapeutic Identification of High-Risk Acute Myeloid Leukemia (AML) Patients from . . . , Clinical Cytometry, Feb. 17, 2003, 4-10, 53B, Wiley-Liss, Inc., US.
Vallier, et al., Activin/Nodal and FGF Pathways Cooperate to Maintain Pluripotency of Human Embryonic Stem Cells, Journal of Cell Sciences, 2005, pp. 4495-4509, vol. 118.
Van Der Greef et al., Rescuing drug discovery: in vivo systems pathology and systems pharmacology, Nature, Dec. 1, 2005, 961-967, 4-1, Nature Reviews, US.
Van Der Windt, et al., The Chioce of Anatomical Site for Islet Transplantation, Cell Transplantation, 2008, pp. 1005-1014, vol. 17.
Van Kooten, et al., Plasma-Treated Polystyrene Surfaces: Model Surfaces for Studying Cell-Biomaterial Interactions, Biomaterials, 2004, pp. 1735-1747, vol. 25.
Van Wachem, et al., Vacuum Cell Seeding: A New Method for the Fast Application of an Evenly Distributed Cell Layer on Porous Vascular Grafts, Biomaterials, 1990, pp. 602-606, vol. 11.
Vanderford et al., Multiple kinases regulate mafA expression in the pancreatic beta cell line MIN6, Biochemistry and Biophysics, 2008, 138-142, 480, Elsevier.
Vodicka, et al., The Miniature Pig as an Animal Model in Biomedical Research, Annals New York Academy of Sciences, 2005, pp. 161-171, vol. 1049.
Vunjak-Novakovic, et al., Dynamic Cell Seeding of Polymer Scaffolds for Cartilage Tissue Engineering, Biotechnology Program, 1998, pp. 193-202, vol. 14, Issue 2.
Wang et al., Relationship of Chemical Structurs of Anthraquinones with their Effects onthe Suppression of Immune Responses, International Journal of Immunopharmacology, 1987, 733-739, 9-6, International Society for Immunopharmacology, GB.
Watanabe, et al., A Rock Inhibitor Permits Survival of Dissociated Human Embryonic Stem Cells, Nature Biotechnology, 2007, pp. 681-686, vol. 25, No. 6.
Wei et al., Cdk5-dependent regulation of glucose-stimulated insulin secretion, Nature Medicine, Sep. 11, 2005, 1104-1108, 11-10, Nature Publishing Group.
Wei, et al., Human Amnion-Isolated Cells Normalize Blood Glucose in Strepozotocin Induced Diabetic Mice, Cell Transplantation, 2003, pp. 545-552, vol. 12, No. 5.
Wei, et al., Transcriptome Profiling of Human and Murine ESCs Identifies Divergent Paths Required to Maintain the Stem Cell State, Stem Cells, 2005, pp. 166-185, vol. 23.

Wells, et al., Early Mouse Endoderm is Patterned by Soluble Factors from Adjacent Germ Layers, Development, 2000, pp. 1563-1572, vol. 127, Issue 8.
Wernig, et al., c-Myc is Dispensable for Direct Reprogramming of Mouse Fibroblasts, Cell Stem Cell, Jan. 2008, pp. 10-12, vol. 2.
Wiles et al., Embryonic Stem Cell Development in a Chemically Defined Medium, Experimental Cell Research, 1999, 241-248, 247, Academic Press.
Wilson, et al., The HMG Box Transcription Factor Sox4 Contributes to the Development of the Endcrine Pancreas, Diabetes, 2005, pp. 3402-4309, vol. 54, Issue 12.
XP002553616_1989, RecName: Full=lnhibin beta B Chain; AltName: Full=Activin beta-B chain; Flags; Precurso, Database UniProt [Online], Jul. 1, 1989, Database Accession No. P09529, EBI Accession No. Uniprot: P09529.
Xu' et al., Basic FGF and Suppression of BMP Signalling Sustain Undifferentiated Proliferation of Human ES Cells, Nature Methods, 2005, pp. 185-189, vol. 2, Issue 3.
Yang et al., Novel cell immobilization method utilizing centrifugal force to achieve high-density hepatocyte culture in porous scaffold, Journal of Biomed Materials Research, Feb. 27, 2001, 379-386, 55, John Wiley & Sons, Inc.
Yang, et al., Survival of Pancreatic Islet Xenografts in NOD Mice with the Theracyte Device, Transplantation Proceedings, 2002, pp. 3349-3350, vol. 34.
Yasuda, et al., Development of Cystic Embryoid Bodies with Visceral Yolk-Sac-Like Structures from Mouse Embryonic Stem Cells Using Low-Adherence 96-Well Plate, Journal of Bioscience and Bioengineering, Apr. 4, 2009, pp. 442-446, vol. 107, No. 4.
Yoneda, et al., The Rho Kinases I and II Regulate Different Aspects of Myosin II Acitivity, The Journal of Cell Biology, 2005, pp. 443-445, vol. 170, No. 3.
Young, et al., Three-Dimensional Culture of Human Uterine Smooth Muscle Nyocytes on a Resorbably Scaffolding, Tissue Engineering, 2003, pp. 451-459, vol. 9, No. 3.
Yu, et al., Induced Pluripotent Stem Cell Lines Derived from Human Somatic Cells, Science, Dec. 21, 2007, pp. 1917-1920, vol. 318.
Yu, et al., Isolation of a Novel Population of Multipotent Adult Stem Cells from Human Hair Follicles, American Journal of Pathology, Jun. 6, 2006, pp. 1879-1888, vol. 168, No. 6.
Zembower, et al., Peptide Boronic Acids Versatile Synthetic Ligands for Affinity Chromatography of Serine Proteinases, International Journal Peptide Protein, 1996, pp. 405-413, vol. 47.
Zhang et al., MafA is a Key Regulator of Glucose-Stimulated Insulin Secretion, Molecular and Cellular Biology, Jun. 2005, 4969-4976, 25-12, American Society for Microbiology.
Zhang, et al., Differentiation Potential of Bone Marrow Mesenchymal Stem Cells into Retina in Normal and Laser-Injured Rat Eye, Science in China Series, 2004, pp. 241-250, vol. 47, No. 3.
Zhang, Jie, The Differentiation of Bone Marrow Mesenchymal Stem Cells into Retina in Rat Eye and the Therapeutical Effect on Severe Injured Retina, A Doctoral Thesis of Chinese PLA Acadamy of Military Medical Sciences, 2003, 1-127, 1-127 (with English Abstract).
Zhang et al, Highly Efficient Differentiation of Human ES Cells and iPS Cells into Mature Pancreatic Insulin-Producing Cells, Cell Research, 2009, pp. 429-438, vol. 19, Issue 14.
Zhao et al., The Islet B Cell-enriched MafA Activator is a Key Regulator of Insulin Gene Transcription, Journal of Biological Chemistry, Mar. 25, 2005, 11887-11894, 280-12, The Amerian Society for Biochemistry and molecular Biology, Inc.
Zhao, et al., Derivation and Characterization of Hepatic Progenitor Cells from Human Embryonic Stem Cells, PLoS One Hepatic Progenitors from hESCs, Jul. 2009, e6468 pp. 1-10, vol. 4, Issue 7.
Zorn, et al., Vertebrate Endoderm Development and Organ Formation, Annual Review Cell Development Biology, 2009, pp. 221-251, vol. 25.
Zubaty, et al., Transplantation of Mesenchymal Stem Cells into RCS Rats for Retinal Repair, Investigative Ophthalmology and Visual Science, 2005, pp. 4160-B518, vol. 46, Supplement S.

\* cited by examiner hES Cell Clusters

Differentiation to DE

Differentiation to PE hES Single Cells, H9scp22

Pluripotency Analysis

H9scp20 Chromosome Spread

Evaluation of Definitive Endoderm Marker Expression

Expression of Pancreatic Markers

Single hES Cell DE Differentiation on MEFs

Differentiation of Single hES Cells in 96 Well Plate

Single hES Cells Identify New Compounds

Transfection Efficiency

SINGLE PLURIPOTENT STEM CELL CULTURE

CROSS REFERENCE TO RELATED APPLICATIONS

This application claims the benefit of U.S. Provisional Application No. 60/947,444, filed on Jul. 1, 2007, which is incorporated by reference herein in its entirety.

The present invention relates to the field of pluripotent stem cell culture and methods to facilitate pluripotent stem cell culture at industrial levels.

BACKGROUND

Pluripotent stem cells, such as, for example, embryonic stem cells have the ability to differentiate into all adult cell types. As such, embryonic stem cells may be a source of replacement cells and tissue for organs that have been damaged as a result of disease, infection, or congenital abnormalities. The potential for embryonic stem cells to be employed as a replacement cell source is hampered by the difficulty of propagating the cells in vitro while maintaining their pluripotency.

Current methods of culturing undifferentiated embryonic stem cells require complex culture conditions, such as, for example, culturing the embryonic stem cells in the presence of a feeder cell layer. Alternatively, media obtained by exposure to feeder cell cultures may be used to culture embryonic stem cells. Culture systems that employ these methods often use cells obtained from a different species than that of the stem cells being cultivated (xenogeneic cells). Additionally, these culture systems may be supplemented with animal serum.

For example, Reubinoff et al (Nature Biotechnology 18: 399-404 (2000)) and Thompson et al (Science 6 Nov. 1998: Vol. 282. no. 5391, pp. 1145-1147) disclose the culture of embryonic stem cell lines from human blastocysts using a mouse embryonic fibroblast feeder cell layer.

In another example, WO2005014799 discloses conditioned medium for the maintenance, proliferation and differentiation of mammalian cells. WO2005014799 state: "The culture medium produced in accordance with the present invention is conditioned by the cell secretion activity of murine cells, in particular, those differentiated and immortalized transgenic hepatocytes, named MMH (Met Murine Hepatocyte)."

However, the use of xenogeneic cells, or xenogeneic cell products, increases the risk that the resulting embryonic stem cell populations produced by such methods may be contaminated viral and/or xeno proteins of immunogenic nature.

Richards et al, (Stem Cells 21: 546-556, 2003) evaluated a panel of 11 different human adult, fetal and neonatal feeder cell layers for their ability to support human embryonic stem cell culture. Richards et a/, states: "human embryonic stem cell lines cultured on adult skin fibroblast feeders retain human embryonic stem cell morphology and remain pluripotent".

U.S. Pat. No. 6,642,048 discloses media that support the growth of primate pluripotent stem (pPS) cells in feeder-free culture, and cell lines useful for production of such media. U.S. Pat. No. 6,642,048 states: "This invention includes mesenchymal and fibroblast-like cell lines obtained from embryonic tissue or differentiated from embryonic stem cells. Methods for deriving such cell lines, processing media, and growing stem cells using the conditioned media are described and illustrated in this disclosure."

US20020072117 discloses cell lines that produce media that support the growth of primate pluripotent stem cells in feeder-free culture. The cell lines employed are mesenchymal and fibroblast-like cell lines obtained from embryonic tissue or differentiated from embryonic stem cells. US20020072117 also discloses the use of the cell lines as a primary feeder cell layer.

In another example, Wang et al (Stem Cells 23: 1221-1227, 2005) disclose methods for the long-term growth of human embryonic stem cells on feeder cell layers derived from human embryonic stem cells.

In another example, Xu et al (Stem Cells 22: 972-980, 2004) disclose conditioned medium obtained from human embryonic stem cell derivatives that have been genetically modified to over-express human telomerase reverse transcriptase.

In another example, Stojkovic et al (Stem Cells 2005 23: 306-314, 2005) disclose a feeder cell system derived from the spontaneous differentiation of human embryonic stem cells.

In a further example, Miyamoto et al (Stem Cells 22: 433-440, 2004) disclose a source of feeder cells obtained from human placenta.

Amit et al (Biol. Reprod 68: 2150-2156, 2003) disclose a feeder cell layer derived from human foreskin.

In another example, Inzunza et al (Stem Cells 23: 544-549, 2005) disclose a feeder cell layer from human postnatal foreskin fibroblasts.

An alternative culture system employs serum-free medium supplemented with growth factors capable of promoting the proliferation of embryonic stem cells. For example, Cheon et al (BioReprod DOI: 10.1095/biolreprod.105.046870, Oct. 19, 2005) disclose a feeder-free, serum-free culture system in which embryonic stem cells are maintained in unconditioned serum replacement (SR) medium supplemented with different growth factors capable of triggering embryonic stem cell self-renewal.

In another example, Levenstein et al (Stem Cells 24: 568-574, 2006) disclose methods for the long-term culture of human embryonic stem cells in the absence of fibroblasts or conditioned medium, using media supplemented with bFGF.

In another example, US20050148070 discloses a method of culturing human embryonic stem cells in defined media without serum and without fibroblast feeder cells, the method comprising: culturing the stem cells in a culture medium containing albumin, amino acids, vitamins, minerals, at least one transferrin or transferrin substitute, at least one insulin or insulin substitute, the culture medium essentially free of mammalian fetal serum and containing at least about 100 ng/ml of a fibroblast growth factor capable of activating a fibroblast growth factor signaling receptor, wherein the growth factor is supplied from a source other than a fibroblast feeder layer, the medium supporting the proliferation of stem cells in an undifferentiated state without feeder cells or conditioned medium.

In another example, US20050233446 discloses a defined media useful in culturing stem cells, including undifferentiated primate primordial stem cells. In solution, the media is substantially isotonic as compared to the stem cells being cultured. In a given culture, the particular medium comprises a base medium and an amount of each of bFGF, insulin, and ascorbic acid necessary to support substantially undifferentiated growth of the primordial stem cells.

In another example, U.S. Pat. No. 6,800,480 states "In one embodiment, a cell culture medium for growing primate-derived primordial stem cells in a substantially undifferentiated state is provided which includes a low osmotic pressure, low endotoxin basic medium that is effective to support the growth of primate-derived primordial stem cells. The basic medium is combined with a nutrient serum effective to support the growth of primate-derived primordial stem cells and a substrate selected from the group consisting of feeder cells and an extracellular matrix component derived from feeder cells. The medium further includes non-essential amino acids, an anti-oxidant, and a first growth factor selected from the group consisting of nucleosides and a pyruvate salt."

In another example, US20050244962 states: "In one aspect the invention provides a method of culturing primate embryonic stem cells. One cultures the stem cells in a culture essentially free of mammalian fetal serum (preferably also essentially free of any animal serum) and in the presence of fibroblast growth factor that is supplied from a source other than just a fibroblast feeder layer. In a preferred form, the fibroblast feeder layer, previously required to sustain a stem cell culture, is rendered unnecessary by the addition of sufficient fibroblast growth factor."

In a further example, WO2005065354 discloses a defined, isotonic culture medium that is essentially feeder-free and serum-free, comprising: a) a basal medium; b) an amount of bFGF sufficient to support growth of substantially undifferentiated mammalian stem cells; c) an amount of insulin sufficient to support growth of substantially undifferentiated mammalian stem cells; and d) an amount of ascorbic acid sufficient to support growth of substantially undifferentiated mammalian stem cells.

In another example, WO2005086845 discloses a method for maintenance of an undifferentiated stem cell, said method comprising exposing a stem cell to a member of the transforming growth factor-beta (TGFβ) family of proteins, a member of the fibroblast growth factor (FGF) family of proteins, or nicotinamide (NIC) in an amount sufficient to maintain the cell in an undifferentiated state for a sufficient amount of time to achieve a desired result.

Embryonic stem cells provide a potential resource for research and drug screening. At present, large-scale culturing of human ES cell lines is problematic and provides substantial challenges. A possible solution to these challenges is to passage and culture the human embryonic stem cells as single cells. Single cells are more amenable to standard tissue culture techniques, such as, for example, counting, transfection, and the like.

For example, Nicolas et al provide a method for producing and expanding hES cell lines from single cells that have been isolated by fluorescence-activated cell sorting (FACS) following genetic modification by lentivirus vectors. Stem Cells and Development (2007), 16(1), 109-118.

In another example, US patent application US2005158852 discloses a method "for improving growth and survival of single human embryonic stem cells. The method includes the step of obtaining a single undifferentiated HES cell; mixing the single undifferentiated cell with an extracellular matrix (ECM) to encompass the cell; and inoculating the mixture onto feeder cells with a nutrient medium in a growth environment".

In another example, Sidhu, K S et al (Stem Cells Dev. 2006 February; 15(1):61-9.) 'describe the first report of three human embryonic stem cell (hESC) clones, hES 3.1, 3.2 and 3.3, that derived from the parent line hES3 by sorting of single-cell preparations by flow cytometry. The viability of single-cell preparations before and after cell sorting remained >98%".

However, passage and culture of human embryonic stem cells as single cells leads to genetic abnormalities and the loss of pluripotency. Culture conditions are important in the maintenance of pluripotency and genetic stability. Generally, passage of hES cell lines is conducted manually or with enzymatic agents such as collagenase, liberase or dispase.

For example, Draper J S et al. note the presence of "karyotypic changes involving the gain of chromosome 17q in three independent human embryonic stem cell lines on five independent occasions." (Nat Biotechnol. 2004 January; 22(1): 53-4. Epub Dec. 7, 2003).

In another example, Buzzard et al. state, "we have only ever detected one karyotype change event . . . the culture methods used may have had some bearing on our results, given that our methods are distinctly different from those used by most other groups. Typically we passage human ES cells after 7 days by first dissecting the colony with the edge of a broken pipette . . . . No enzymic or chemical methods of cell dissociation are incorporated into this method. We speculate that this may explain the relative cytogenetic resilience of hES cells in our hands." (Nat Biotechnol. 2004 April; 22(4):381-2; author reply 382).

In another example, Mitalipova M M et al state "bulk passage methods . . . can perpetuate aneuploid cell populations after extended passage in culture, but may be used for shorter periods (up to at least 15 passages) without compromising the karyotypes . . . it may be possible to maintain a normal karyotype in hES cells under long-term manual propagation conditions followed by limited bulk passaging in experiments requiring greater quantities of hES cells than manual passage methods, alone, can provide". (Nat Biotechnol. 2005 January; 23(1):19-20).

In another example, Heng B C et al state "the results demonstrated that the second protocol (trypsinization with gentle pipetting) is much less detrimental to cellular viability than is the first protocol (collagenase treatment with scratching). This in turn translated to higher freeze-thaw survival rates". (Biotechnology and Applied Biochemistry (2007), 47(1), 33-37).

In another example, Hasegawa K. et at state, "we have established hESC sublines tolerant of complete dissociation. These cells exhibit high replating efficiency and also high cloning efficiency and they maintain their ability to differentiate into the three germ layers."(Stem Cells. 2006 Dec;24 (12):2649-60. Epub Aug. 24, 2006). Hasegawa, K et al further state that "after dissociation into the single cells, hESCs exhibit decreased survival and self-renewal as well as a low replating efficiency." Hasegawa, K. et al also state that "24 hours after seeding, the attached and surviving cells were very low in number (approximately 15%), and many floating cells and debris were present in culture for hESCs with the lowest replating efficiencies (phase 1). This was similar to that for the normal hESCs. However, for sublines with greater replating efficiencies (phases 2 and 3), most cells were attached and alive (>85%), and the number of floating cells and the amount of debris were low."

SUMMARY

The present invention provides methods for the maintenance, passage and differentiation of pluripotent stem cells that have been released as single cells using enzymes. In particular, the present invention provides methods for the maintenance, passage and differentiation of pluripotent stem cells that have been released as single cells with no subsequent loss in pluripotency, and no gain of chromosomal abnormalities.

In one embodiment, the present invention provides a method for differentiating pluripotent stem cells, comprising the steps of:
  a) Culturing pluripotent stem cells as clusters,
  b) Releasing the pluripotent stem cells as single cells,
  c) Plating the single pluripotent stem cells on a tissue culture substrate, and
  d) Differentiating the cells.

In one embodiment, the present invention provides a method for maintaining pluripotent stem cells, comprising the steps of:
a) Obtaining pluripotent stem cells,
b) Releasing the pluripotent stem cells as single cells, and
c) Plating the single pluripotent stem cells on a tissue culture substrate.

In one embodiment, the present invention provides a method for passaging pluripotent stem cells, comprising the steps of:
a) Obtaining clusters of pluripotent stem cells,
b) Releasing the pluripotent stem cells as single cells,
c) Plating the single pluripotent stem cells on a tissue culture substrate,
d) Allowing the single pluripotent stem cells to expand,
e) Releasing the single pluripotent stem cells, and
f) Plating the single pluripotent stem cells on a new tissue culture substrate.

DETAILED DESCRIPTION

Figure 1:
FIG. 1: An image at 4× enlargement of H9 ccp33 human ES cells grown on 1:30 reduced growth factor MATRIGEL™ in MEF-conditioned medium.

For clarity of disclosure, and not by way of limitation, the detailed description of the invention is divided into the following subsections that describe or illustrate certain features, embodiments or applications of the present invention.

Definitions

Stem cells are undifferentiated cells defined by their ability at the single cell level to both self-renew and differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Stem cells are classified by their developmental potential as: (1) totipotent, meaning able to give rise to all embryonic and extraembryonic cell types; (2) pluripotent, meaning able to give rise to all embryonic cell types; (3) multipotent, meaning able to give rise to a subset of cell lineages, but all within a particular tissue, organ, or physiological system (for example, hematopoietic stem cells (HSC) can produce progeny that include HSC (self-renewal), blood cell restricted oligopotent progenitors and all cell types and elements (e.g., platelets) that are normal components of the blood); (4) oligopotent, meaning able to give rise to a more restricted subset of cell lineages than multipotent stem cells; and (5) unipotent, meaning able to give rise to a single cell lineage (e.g., spermatogenic stem cells).

Differentiation is the process by which an unspecialized ("uncommitted") or less specialized cell acquires the features of a specialized cell such as, for example, a nerve cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

Various terms are used to describe cells in culture. "Maintenance" refers generally to cells placed in a growth medium under conditions that facilitate cell growth and/or division, that may or may not result in a larger population of the cells. "Passaging" refers to the process of removing the cells from one culture vessel and placing them in a second culture vessel under conditions that facilitate cell growth and/or division.

A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but not limited to the seeding density, substrate, medium, growth conditions, and time between passaging.

"AFP" or "alpha-fetoprotein protein" as used herein, refers to an antigen produced at the onset of liver development. AFP may also be expressed in extraembryonic cells.

"β-cell lineage" refer to cells with positive gene expression for the transcription factor PDX-1 and at least one of the following transcription factors: NGN-3, Nkx2.2, Nkx6.1, NeuroD, Isl-1, HNF-3 beta, MAFA, Pax4, and Pax6. Cells expressing markers characteristic of the β cell lineage include β cells.

"Brachyury", as used herein, is a T-box gene family member. It is the marker for primitive streak and mesoderm cells.

"Cells expressing markers characteristic of the definitive endoderm lineage" as used herein refer to cells expressing at least one of the following markers: SOX-17, GATA-4, HNF-3 beta, GSC, Cerl, Nodal, FGF8, Brachyury, Mix-like homeobox protein, FGF4 CD48, eomesodermin (EOMES), DKK4, FGF17, GATA-6, CXCR4, C-Kit, CD99, or OTX2. Cells expressing markers characteristic of the definitive endoderm lineage include primitive streak precursor cells, primitive streak cells, mesendoderm cells and definitive endoderm cells.

"CD99" as used herein refers to the protein encoded by the gene with the accession number NM_002414.

"Cells expressing markers characteristic of the pancreatic endoderm lineage" as used herein refer to cells expressing at least one of the following markers: PDX-1, HNF-1beta, PTF-1 alpha, HNF-6, or HB9. Cells expressing markers characteristic of the pancreatic endoderm lineage include pancreatic endoderm cells.

"Cells expressing markers characteristic of the pancreatic endocrine lineage" as used herein refer to cells expressing at least one of the following markers: NGN-3, NeuroD, Islet-1, PDX-1, NKX6.1, Pax-4, or PTF-1 alpha. Cells expressing markers characteristic of the pancreatic endocrine lineage include pancreatic endocrine cells, pancreatic hormone expressing cells, and pancreatic hormone secreting cells, and cells of the β-cell lineage.

"CXCR4" as used herein refers to the stromal cell-derived factor 1 (SDF-1) receptor, also known as "LESTR" or "fusin". In the gastrulating mouse embryo, CXCR4 is expressed in the definitive endoderm and mesoderm but not in extraembryonic endoderm.

"Definitive endoderm" as used herein refers to cells which bear the characteristics of cells arising from the epiblast during gastrulation and which form the gastrointestinal tract and its derivatives. Definitive endoderm cells express the following markers: CXCR4, HNF-3 beta, GATA-4, SOX-17, Cerberus, OTX2, goosecoid, c-Kit, CD99, and Mix11.

"Extraembryonic endoderm" as used herein refers to a population of cells expressing at least one of the following markers: SOX-7, AFP, and SPARC.

"GATA-4" and "GATA-6" are members of the GATA transcription factor family. This family of transcription factors is induced by TGF-β signaling and contributes to the maintenance of early endoderm markers.

"GLUT-2", as used herein, refers to the glucose transporter molecule that is expressed in numerous fetal and adult tissues, including pancreas, liver, intestine, brain, and kidney.

"Goosecoid" or "GSC" as used herein, refers to a homeodomain transcription factor expressed in the dorsal lip of the blastopore.

"Islet-1" or "Isl-1" as used herein is a member of the LIM/homeodomain family of transcription factors, and is expressed in the developing pancreas.

"MafA" as used herein is a transcription factor expressed in the pancreas, and controls the expression of genes involved in insulin biosynthesis and secretion.

"Markers" as used herein, are nucleic acid or polypeptide molecules that are differentially expressed in a cell of interest. In this context, differential expression means an increased level for a positive marker and a decreased level for a negative marker. The detectable level of the marker nucleic acid or polypeptide is sufficiently higher or lower in the cells of interest compared to other cells, such that the cell of interest can be identified and distinguished from other cells using any of a variety of methods known in the art.

"Mesendoderm cell" as used herein refers to a cell expressing at least one of the following markers: CD48, eomesodermin (EOMES), SOX-17, DKK4, HNF-3 beta, GSC, FGF17, GATA-6.

"Nodal" as used herein, is a member of the TGF beta superfamily of proteins.

"Oct-4" is a member of the POU-domain transcription factor and is widely regarded as a hallmark of pluripotent stem cells. The relationship of Oct-4 to pluripotent stem cells is indicated by its tightly restricted expression to undifferentiated pluripotent stem cells. Upon differentiation to somatic lineages, the expression of Oct-4 disappears rapidly.

"Pancreatic endocrine cell" or "pancreatic hormone expressing cell" as used herein refers to a cell capable of expressing at least one of the following hormones: insulin, glucagon, somatostatin, and pancreatic polypeptide.

"Pancreatic hormone secreting cell" as used herein refers to a cell capable of secreting at least one of the following hormones: insulin, glucagon, somatostatin, and pancreatic polypeptide.

"Pax-4" and "Pax-6" as used herein are pancreatic β cell specific transcription factors that are implicated in islet development.

"PDX-1" as used herein refers to a homeodomain transcription factor implicated in pancreas development.

"Pre-primitive streak cell" as used herein refers to a cell expressing at least one of the following markers: Nodal, or FGF8.

"Primitive streak cell" as used herein refers to a cell expressing at least one of the following markers: Brachyury, Mix-like homeobox protein, or FGF4.

"PTF-1 alpha" as used herein refers to a basic helix-loop-helix protein of 48 kD that is a sequence-specific DNA-binding subunit of the trimeric pancreas transcription factor-1 (PTF1).

"SPARC" as used herein is also known as "secreted protein acidic and rich in cysteine".

"SSEA-1" (Stage Specific Embryonic Antigen-1) is a glycolipid surface antigen present on the surface of murine teratocarcinoma stem cells (EC), murine and human embryonic germ cells (EG), and murine embryonic stem cells (ES).

"SSEA-3" (Stage Specific Embryonic Antigen-3) is a glycolipid surface antigen present on the surface of human teratocarcinoma stem cells (EC), human embryonic germ cells (EG), and human embryonic stem cells (ES).

"SSEA-4" (Stage Specific Embryonic Antigen-4) is a glycolipid surface antigen present on the surface of human teratocarcinoma stem cells (EC), human embryonic germ cells (EG), and human embryonic stem cells (ES).

"TRA1-60" is a keratin sulfate related antigen that is expressed on the surface of human teratocarcinoma stem cells (EC), human embryonic germ cells (EG), and human embryonic stem cells (ES).

"TRA1-81" is a keratin sulfate related antigen that is expressed on the surface of human teratocarcinoma stem cells (EC), human embryonic germ cells (EG), and human embryonic stem cells (ES).

"TRA2-49" is an alkaline phosphatase isozyme expressed on the surface of human teratocarcinoma stem cells (EC) and human embryonic stem cells (ES).

The present invention provides methods for the maintenance, passage and differentiation of pluripotent stem cells that have been released as single cells using enzymes. In particular, the present invention provides methods for the maintenance, passage and differentiation of pluripotent stem cells that have been released as single cells with no subsequent loss in pluripotency, and no gain of chromosomal abnormalities.

In one embodiment, the present invention provides a method for differentiating pluripotent stem cells, comprising the steps of:
  a) Culturing the pluripotent stem cells as clusters,
  b) Releasing the pluripotent stem cells as single cells,
  c) Plating the single pluripotent stem cells on a tissue culture substrate, and
  d) Differentiating the single pluripotent stem cells.

The clusters of pluripotent stem cells may be released as single cells by enzymatic treatment. The enzymatic treatment may be by TrypLE™Express (stable trypsin-like enzyme (Invitrogen (Carlsbad, CA)), alternatively by TrypLE™Select (animal origin-free trypsin-like enzyme (Invitrogen (Carlsbad, CA)), alternatively by Trypsin, or alternatively by Trypsin/EDTA.

The enzymatic treatment may be for about two to about five minutes. Alternatively, the enzymatic treatment is for about five minutes.

The enzymes may be used at a concentration from about 0.5 g/L to about 2.5 g/L enzyme.

In one embodiment, the clusters of pluripotent stem cells are released as single cells using TrypLE™EXPRESS.

In one embodiment, the pluripotent stem cells are embryonic stem cells. In an alternate embodiment, the embryonic stem cells are human.

In one embodiment, the released single pluripotent cells are plated on a tissue culture substrate. The substrate may be MATRIGEL™, alternatively the substrate may be fibronectin, alternatively the substrate may be laminin, alternatively the substrate may be human serum, or alternatively the substrate may be collagen.

In one embodiment, the released single pluripotent cells are plated on a three dimensional support. The support may be incorporated with at least one pharmaceutical agent that facilitates the survival and function of the released single pluripotent cells. Support materials suitable for use for purposes of the present invention include synthetic and natural materials in the form of foams, sponges, gels, hydrogels, textiles, and nonwoven structures.

In one embodiment the tissue culture substrate is MATRIGEL™. The MATRIGEL™ may be used at a dilution from about 1:30 to about 1:10. In one embodiment, the MATRIGEL™ is used at a dilution of 1:10.

The single pluripotent stem cells may be differentiated into cells expressing markers characteristic of the definitive endoderm lineage. Alternatively, the single pluripotent stem cells may be differentiated into cells expressing markers characteristic of the pancreatic endoderm lineage. Alternatively, the single pluripotent stem cells may be differentiated into cells expressing markers characteristic of the pancreatic endocrine lineage.

In one embodiment, the present invention provides a method for maintaining pluripotent stem cells, comprising the steps of:
  a) Obtaining clusters of pluripotent stem cells,
  b) Releasing the pluripotent stem cells as single cells, and
  c) Plating the single pluripotent stem cells on a tissue culture substrate.

The clusters of pluripotent stem cells may be released as single cells by enzymatic treatment. The enzymatic treatment may be by TrypLE™ Express, alternatively by TrypLE™Select, alternatively by Trypsin, or alternatively by Trypsin/EDTA.

The enzymatic treatment may be for about two to about five minutes. Alternatively, the enzymatic treatment is for about five minutes.

The enzymes may be used at a concentration from about 0.5 g/L to 2.5 g/L enzyme.

In one embodiment, the clusters of pluripotent stem cells are released as single cells using TrypLE™ Express.

In one embodiment, the pluripotent stem cells are embryonic stem cells. In an alternate embodiment, the embryonic stem cells are human.

In one embodiment, the released, single, pluripotent cells are plated on a tissue culture substrate. The substrate may be MATRIGEL™, alternatively, the substrate may be growth factor-reduced MATRIGEL™, alternatively the substrate may be fibronectin, alternatively the substrate may be laminin, alternatively the substrate may be human serum, or alternatively the substrate may be collagen.

In one embodiment, the released single pluripotent cells are plated on a three dimensional support. The support may be incorporated with at least one pharmaceutical agent that facilitates the survival and function of the released single pluripotent cells. Support materials suitable for use for purposes of the present invention include synthetic and natural materials in the form of foams, sponges, gels, hydrogels, textiles, and nonwoven structures.

In one embodiment, the tissue culture substrate is growth factor-reduced MATRIGEL™. The growth factor-reduced MATRIGEL™ may be used at a dilution from about 1:30 to about 1:10. In one embodiment, the MATRIGEL™ is used at a dilution of 1:30.

The single pluripotent stem cells may be differentiated into cells expressing markers characteristic of the definitive endoderm lineage. Alternatively, the single pluripotent stem cells may be differentiated into cells expressing markers characteristic of the pancreatic endoderm lineage. Alternatively, the single pluripotent stem cells may be differentiated into cells expressing markers characteristic of the pancreatic endocrine lineage.

In one embodiment, the present invention provides a method for passaging pluripotent stem cells, comprising the steps of:
a) Obtaining clusters of pluripotent stem cells,
b) Releasing the pluripotent stem cells as single cells,
c) Plating the single pluripotent stem cells on a tissue culture substrate,
d) Allowing the single pluripotent stem cells to expand,
e) Releasing the single pluripotent stem cells, and
f) Plating the single pluripotent stem cells on a new tissue culture substrate.

The clusters of pluripotent stem cells may be released as single cells by enzymatic treatment. The enzymatic treatment may be by TrypLE™ Express, alternatively by TrypLE™ Select, alternatively by Trypsin, or alternatively by Trypsin/EDTA.

The enzymatic treatment may be for about two to about five minutes. Alternatively, the enzymatic treatment is for about five minutes. The enzymes may be used at a concentration from about 0.5 g/L to 2.5 g/L enzyme.

In one embodiment, the clusters of pluripotent stem cells are released as single cells using TrypLE™ Express.

In one embodiment, the single pluripotent cells are grown to a density of about 70 to 80% before cells are again subjected to enzymatic passaging onto a new tissue culture substrate. The single pluripotent stem cells may be passaged once, or they may be passaged more than once using the methods of the present invention.

In one embodiment, the pluripotent stem cells are embryonic stem cells. In an alternate embodiment, the embryonic stem cells are human.

In one embodiment, the released single pluripotent cells are plated on a tissue culture substrate. The substrate may be MATRIGEL™, alternatively, the substrate may be growth factor-reduced MATRIGEL™, alternatively the substrate may be fibronectin, alternatively the substrate may be laminin, alternatively the substrate may be human serum or alternatively the substrate may be collagen.

In one embodiment, the released single pluripotent cells are plated on a three dimensional support. The support may be incorporated with at least one pharmaceutical agent that facilitates the survival and function of the released single pluripotent cells. Support materials suitable for use for purposes of the present invention include synthetic and natural materials in the form of foams, sponges, gels, hydrogels, textiles, and nonwoven structures.

In one embodiment, the tissue culture substrate is growth factor-reduced MATRIGEL™. The growth factor-reduced MATRIGEL™ may be used at a dilution from about 1:30 to about 1:10. In one embodiment, the MATRIGEL™ is used at a dilution of 1:30.

Other Methods for Isolation, Expansion and Culture of Pluripotent Stem Cells

Characterization of Pluripotent Stem Cells

Pluripotent stem cells may express one or more of the stage-specific embryonic antigens (SSEA) 3 and 4, and markers detectable using antibodies designated Tra-1-60 and Tra-1-81 (Thomson et al., Science 282:1145, 1998). Differentiation of pluripotent stem cells in vitro results in the loss of SSEA-4, Tra-1-60, and Tra-1-81 expression (if present) and increased expression of SSEA-1. Undifferentiated pluripotent stem cells typically have alkaline phosphatase activity, which can be detected by fixing the cells with 4% paraformaldehyde and then developing with Vector Red as a substrate, as described by the manufacturer (Vector Laboratories, Burlingame Calif.) Undifferentiated pluripotent stem cells also typically express Oct-4 and TERT, as detected by RT-PCR.

Another desirable phenotype of propagated pluripotent stem cells is a potential to differentiate into cells of all three germinal layers: endoderm, mesoderm, and ectoderm tissues. Pluripotency of stem cells can be confirmed, for example, by injecting cells into severe combined immunodeficient (SCID) mice, fixing the teratomas that form using 4% paraformaldehyde, and then examining them histologically for evidence of cell types from the three germ layers. Alternatively, pluripotency may be determined by the creation of embryoid bodies and assessing the embryoid bodies for the presence of markers associated with the three germinal layers.

Propagated pluripotent stem cell lines may be karyotyped using a standard G-banding technique and compared to published karyotypes of the corresponding primate species. It is desirable to obtain cells that have a "normal karyotype," which means that the cells are euploid, wherein all human chromosomes are present and not noticeably altered.

Sources of Pluripotent Stem Cells

The types of pluripotent stem cells that may be used include established lines of pluripotent cells derived from tissue formed after gestation, including pre-embryonic tissue (such as, for example, a blastocyst), embryonic tissue, or fetal tissue taken any time during gestation, typically but not necessarily before approximately 10-12 weeks gestation. Non-limiting examples are established lines of human embryonic stem cells or human embryonic germ cells, such as, for example the human embryonic stem cell lines H1, H7, and H9 (WiCell). Also contemplated is use of the compositions of this disclosure during the initial establishment or stabilization of such cells, in which case the source cells would be primary pluripotent cells taken directly from the source tissues. Also suitable are cells taken from a pluripotent stem cell population already cultured in the absence of feeder cells. Also suitable are mutant human embryonic stem cell lines, such as, for example, BG01v (BresaGen, Athens, Ga.).

In one embodiment, human embryonic stem cells are prepared as described by Thomson et al. (U.S. Pat. No. 5,843, 780; Science 282:1145, 1998; Curr. Top. Dev. Biol. 38:133 ff., 1998; Proc. Natl. Acad. Sci. U.S.A. 92:7844, 1995).

Culture of Pluripotent Stem Cells

In one embodiment, pluripotent stem cells are typically cultured on a layer of feeder cells that support the pluripotent stem cells in various ways. Alternatively, pluripotent stem cells are cultured in a culture system that is essentially free of feeder cells, but nonetheless supports proliferation of pluripotent stem cells without undergoing substantial differentiation. The growth of pluripotent stem cells in feeder-free culture without differentiation is supported using a medium conditioned by culturing previously with another cell type. Alternatively, the growth of pluripotent stem cells in feeder-free culture without differentiation is supported using a chemically defined medium.

For example, Reubinoff et al (Nature Biotechnology 18: 399-404 (2000)) and Thompson et al (Science 6 Nov. 1998: Vol. 282. no. 5391, pp. 1145-1147) disclose the culture of pluripotent stem cell lines from human blastocysts using a mouse embryonic fibroblast feeder cell layer.

Richards et al, (Stem Cells 21: 546-556, 2003) evaluated a panel of 11 different human adult, fetal and neonatal feeder cell layers for their ability to support human pluripotent stem cell culture. Richards et al, state: "human embryonic stem cell lines cultured on adult skin fibroblast feeders retain human embryonic stem cell morphology and remain pluripotent".

US20020072117 discloses cell lines that produce media that support the growth of primate pluripotent stem cells in feeder-free culture. The cell lines employed are mesenchymal and fibroblast-like cell lines obtained from embryonic tissue or differentiated from embryonic stem cells. US20020072117 also discloses the use of the cell lines as a primary feeder cell layer.

In another example, Wang et al (Stem Cells 23: 1221-1227, 2005) discloses methods for the long-term growth of human pluripotent stem cells on feeder cell layers derived from human embryonic stem cells.

In another example, Stojkovic et al (Stem Cells 2005 23: 306-314, 2005) disclose a feeder cell system derived from the spontaneous differentiation of human embryonic stem cells.

In a further example, Miyamoto et al (Stem Cells 22: 433-440, 2004) disclose a source of feeder cells obtained from human placenta.

Amit et al (Biol. Reprod 68: 2150-2156, 2003) discloses a feeder cell layer derived from human foreskin.

In another example, Inzunza et al (Stem Cells 23: 544-549, 2005) disclose a feeder cell layer from human postnatal foreskin fibroblasts.

U.S. Pat. No. 6,642,048 discloses media that support the growth of primate pluripotent stem (pPS) cells in feeder-free culture, and cell lines useful for production of such media. U.S. Pat. No. 6,642,048 states: "This invention includes mesenchymal and fibroblast-like cell lines obtained from embryonic tissue or differentiated from embryonic stem cells. Methods for deriving such cell lines, processing media, and growing stem cells using the conditioned media are described and illustrated in this disclosure."

In another example, WO2005014799 discloses conditioned medium for the maintenance, proliferation and differentiation of mammalian cells. WO2005014799 states: "The culture medium produced in accordance with the present invention is conditioned by the cell secretion activity of murine cells, in particular, those differentiated and immortalized transgenic hepatocytes, named MMH (Met Murine Hepatocyte)."

In another example, Xu et al (Stem Cells 22: 972-980, 2004) discloses conditioned medium obtained from human embryonic stem cell derivatives that have been genetically modified to over express human telomerase reverse transcriptase.

In another example, US20070010011 discloses a chemically defined culture medium for the maintenance of pluripotent stem cells.

An alternative culture system employs serum-free medium supplemented with growth factors capable of promoting the proliferation of embryonic stem cells. For example, Cheon et al (BioReprod DOI: 10.1095/biolreprod.105.046870, Oct. 19, 2005) disclose a feeder-free, serum-free culture system in which embryonic stem cells are maintained in unconditioned serum replacement (SR) medium supplemented with different growth factors capable of triggering embryonic stem cell self-renewal.

In another example, Levenstein et al (Stem Cells 24: 568-574, 2006) disclose methods for the long-term culture of human embryonic stem cells in the absence of fibroblasts or conditioned medium, using media supplemented with bFGF.

In another example, US20050148070 discloses a method of culturing human embryonic stem cells in defined media without serum and without fibroblast feeder cells, the method comprising: culturing the stem cells in a culture medium containing albumin, amino acids, vitamins, minerals, at least one transferrin or transferrin substitute, at least one insulin or insulin substitute, the culture medium essentially free of mammalian fetal serum and containing at least about 100 ng/ml of a fibroblast growth factor capable of activating a fibroblast growth factor signaling receptor, wherein the growth factor is supplied from a source other than just a fibroblast feeder layer, the medium supporting the proliferation of stem cells in an undifferentiated state without feeder cells or conditioned medium.

In another example, US20050233446 discloses a defined medium useful in culturing stem cells, including undifferentiated primate primordial stem cells. In solution, the medium is substantially isotonic as compared to the stem cells being cultured. In a given culture, the particular medium comprises a base medium and an amount each of bFGF, insulin, and ascorbic acid necessary to support substantially undifferentiated growth of the primordial stem cells.

In another example, U.S. Pat. No. 6,800,480 states, "In one embodiment, a cell culture medium for growing primate-derived primordial stem cells in a substantially undifferentiated state is provided which includes a low osmotic pressure, low endotoxin basic medium that is effective to support the growth of primate-derived primordial stem cells. The basic medium is combined with a nutrient serum effective to support the growth of primate-derived primordial stem cells and a substrate selected from the group consisting of feeder cells and an extracellular matrix component derived from feeder cells. The medium further includes non-essential amino acids, an anti-oxidant, and a first growth factor selected from the group consisting of nucleosides and a pyruvate salt."

In another example, US20050244962 states: "In one aspect the invention provides a method of culturing primate embryonic stem cells. One cultures the stem cells in a culture essentially free of mammalian fetal serum (preferably also essentially free of any animal serum) and in the presence of fibroblast growth factor that is supplied from a source other than just a fibroblast feeder layer. In a preferred form, the fibroblast feeder layer, previously required to sustain a stem cell culture, is rendered unnecessary by the addition of sufficient fibroblast growth factor."

In a further example, WO2005065354 discloses a defined, isotonic culture medium that is essentially feeder-free and serum-free, comprising: a) a basal medium; b) an amount of bFGF sufficient to support growth of substantially undifferentiated mammalian stem cells; c) an amount of insulin sufficient to support growth of substantially undifferentiated mammalian stem cells; and d) an amount of ascorbic acid sufficient to support growth of substantially undifferentiated mammalian stem cells.

In another example, WO2005086845 discloses a method for maintenance of an undifferentiated stem cell, said method comprising exposing a stem cell to a member of the transforming growth factor-beta (TGFβ) family of proteins, a member of the fibroblast growth factor (FGF) family of proteins, or nicotinamide (NIC) in an amount sufficient to maintain the cell in an undifferentiated state for a sufficient amount of time to achieve a desired result.

The pluripotent stem cells may be plated onto a suitable culture substrate. In one embodiment, the suitable culture substrate is an extracellular matrix component, such as, for example, those derived from basement membrane or that may form part of adhesion molecule receptor-ligand couplings. In one embodiment, the suitable culture substrate is MATRIGEL™ (Becton Dickenson). MATRIGEL™ is a soluble preparation from Engelbreth-Holm-Swarm tumor cells that gels at room temperature to form a reconstituted basement membrane.

Other extracellular matrix components and component mixtures are suitable as an alternative. Depending on the cell type being proliferated, this may include laminin, fibronectin, proteoglycan, entactin, heparan sulfate, and the like, alone or in various combinations.

The pluripotent stem cells may be plated onto the substrate in a suitable distribution and in the presence of a medium that promotes cell survival, propagation, and retention of the desired characteristics. All these characteristics benefit from careful attention to the seeding distribution and can readily be determined by one of skill in the art.

Suitable culture media may be made from the following components, such as, for example, Dulbecco's modified Eagle's medium (DMEM), Gibco # 11965-092; Knockout Dulbecco's modified Eagle's medium (KO DMEM), Gibco # 10829-018; Ham's F12/50% DMEM basal medium; 200 mM L-glutamine, Gibco # 15039-027; non-essential amino acid solution, Gibco 11140-050; β-mercaptoethanol, Sigma # M7522; human recombinant basic fibroblast growth factor (bFGF), Gibco # 13256-029.

Differentiation of Pluripotent Stem Cells

In one embodiment of the present invention, pluripotent stem cells are propagated in culture, while maintaining their pluripotency. Changes in pluripotency of the cells with time can be determined by detecting changes in the levels of expression of markers associated with pluripotency. Alternatively, changes in pluripotency can be monitored by detecting changes in the levels of expression of markers associated with differentiation or markers associated with another cell type.

In an alternate embodiment, pluripotent stem cells are propagated in culture and then treated in a manner that promotes their differentiation into another cell type. The other cell type may be a cell expressing markers characteristic of the definitive endoderm lineage. Alternatively, the cell type may be a cell expressing markers characteristic of the pancreatic endoderm lineage. Alternatively, the cell type may be a cell expressing markers characteristic of the pancreatic endocrine lineage. Alternatively, the cell type may be a cell expressing markers characteristic of the β-cell lineage.

Pluripotent stem cells treated in accordance with the methods of the present invention may be differentiated into a variety of other cell types by any suitable method in the art. For example, pluripotent stem cells treated in accordance with the methods of the present invention may be differentiated into neural cells, cardiac cells, hepatocytes, and the like.

For example, pluripotent stem cells treated in accordance with the methods of the present invention may be differentiated into neural progenitors and cardiomyocytes according to the methods disclosed in WO2007030870.

In another example, pluripotent stem cells treated in accordance with the methods of the present invention may be differentiated into hepatocytes according to the methods disclosed in U.S. Pat. No. 6,458,589.

Formation of Cells Expressing Markers Characteristic of the Definitive Endoderm Lineage Pluripotent stem cells may be differentiated into cells expressing markers characteristic of the definitive endoderm lineage by any method in the art.

For example, pluripotent stem cells may be differentiated into cells expressing markers characteristic of the definitive endoderm lineage according to the methods disclosed in D'Amour et al, Nature Biotechnology 23, 1534-1541 (2005).

For example, pluripotent stem cells may be differentiated into cells expressing markers characteristic of the definitive endoderm lineage according to the methods disclosed in Shinozaki et al, Development 131, 1651-1662 (2004).

For example, pluripotent stem cells may be differentiated into cells expressing markers characteristic of the definitive endoderm lineage according to the methods disclosed in McLean et al, Stem Cells 25, 29-38 (2007).

For example, pluripotent stem cells may be differentiated into cells expressing markers characteristic of the definitive endoderm lineage according to the methods disclosed in D'Amour et al, Nature Biotechnology 24, 1392-1401 (2006).

Markers characteristic of the definitive endoderm lineage are selected from the group consisting of SOX17, GATA4, Hnf-3beta, GSC, Cerl, Nodal, FGF8, Brachyury, Mix-like homeobox protein, FGF4 CD48, eomesodermin (EOMES), DKK4, FGF17, GATA6, CXCR4, C-Kit, CD99, and OTX2. Suitable for use in the present invention is a cell that expresses at least one of the markers characteristic of the definitive endoderm lineage. In one aspect of the present invention, a cell expressing markers characteristic of the definitive endoderm lineage is a primitive streak precursor cell. In an alternate aspect, a cell expressing markers characteristic of the definitive endoderm lineage is a mesendoderm cell. In an alternate aspect, a cell expressing markers characteristic of the definitive endoderm lineage is a definitive endoderm cell.

Formation of Cells Expressing Markers Characteristic of the Pancreatic Endoderm Lineage Pluripotent stem cells may be differentiated into cells expressing markers characteristic of the pancreatic endoderm lineage by any method in the art.

For example, pluripotent stem cells may be differentiated into cells expressing markers characteristic of the pancreatic endoderm lineage according to the methods disclosed in D'Amour et al, Nature Biotechnology 24, 1392-1401 (2006).

Markers characteristic of the pancreatic endoderm lineage are selected from the group consisting of Pdx1, HNF-1beta, PTF1a, HNF-6, HB9 and PROX1. Suitable for use in the present invention is a cell that expresses at least one of the markers characteristic of the pancreatic endoderm lineage. In one aspect of the present invention, a cell expressing markers characteristic of the pancreatic endoderm lineage is a pancreatic endoderm cell.

Formation of Cells Expressing Markers of the Pancreatic Endocrine Lineage

Pluripotent stem cells may be differentiated into cells expressing markers characteristic of the pancreatic endocrine lineage by any method in the art.

For example, pluripotent stem cells may be differentiated into cells expressing markers characteristic of the pancreatic endocrine lineage according to the methods disclosed in D'Amour et a/, Nature Biotechnology 24, 1392-1401 (2006).

For example, pluripotent stem cells may be differentiated into cells expressing markers characteristic of the pancreatic endocrine lineage, by the methods disclosed in Nature Biotechnology 24, 1392-1401 (2006).

For example, pluripotent stem cells may be differentiated into cells expressing markers characteristic of the pancreatic endocrine lineage, by the methods disclosed in D' Amour et al, Nature Biotechnology, 2006.

Markers characteristic of the pancreatic endocrine lineage are selected from the group consisting of NGN-3, NeuroD, Islet-1, Pdx-1, NKX6.1, Pax-4, and PTF-1 alpha. In one embodiment, a pancreatic endocrine cell is capable of expressing at least one of the following hormones: insulin, glucagon, somatostatin, and pancreatic polypeptide. Suitable for use in the present invention is a cell that expresses at least one of the markers characteristic of the pancreatic endocrine lineage. In one aspect of the present invention, a cell expressing markers characteristic of the pancreatic endocrine lineage is a pancreatic endocrine cell. The pancreatic endocrine cell may be a pancreatic hormone-expressing cell. Alternatively, the pancreatic endocrine cell may be a pancreatic hormone-secreting cell.

In one aspect of the present invention, the pancreatic endocrine cell is a cell expressing markers characteristic of the β cell lineage. A cell expressing markers characteristic of the β cell lineage expresses Pdx1 and at least one of the following transcription factors: NGN-3, Nkx2.2, Nkx6.1, NeuroD, Isl-1, HNF-3 beta, MAFA, Pax4, and Pax6. In one aspect of the present invention, a cell expressing markers characteristic of the β cell lineage is a β cell.

Three Dimensional Supports

Support materials suitable for use for purposes of the present invention include synthetic and natural materials in the form of foams, sponges, gels, hydrogels, textiles, and nonwoven structures, which have been used in vitro and in vivo to reconstruct or regenerate biological tissue, as well as to deliver chemotactic agents for inducing tissue growth, are suitable for use in practicing the methods of the present invention. See, for example, the materials disclosed in U.S. Pat. Nos. 5,770,417, 6,022,743, 5,567,612, 5,759,830, 6,626,950, 6,534,084, 6,306,424, 6,365,149, 6,599,323, 6,656,488, U.S. Published Application 2004/0062753 A1, U.S. Pat. Nos. 4,557,264 and 6,333,029.

To form a support incorporated with a pharmaceutical agent, the pharmaceutical agent can be mixed with the polymer solution prior to forming the support. Alternatively, a pharmaceutical agent could be coated onto a fabricated support, preferably in the presence of a pharmaceutical carrier. The pharmaceutical agent may be present as a liquid, a finely divided solid, or any other appropriate physical form. Alternatively, excipients may be added to the support to alter the release rate of the pharmaceutical agent. In an alternate embodiment, the support is incorporated with at least one pharmaceutical compound that is an anti-inflammatory compound, such as, for example compounds disclosed in U.S. Pat. No. 6,509,369.

The support may be incorporated with at least one pharmaceutical compound that is an anti-apoptotic compound, such as, for example, compounds disclosed in U.S. Pat. No. 6,793,945.

The support may also be incorporated with at least one pharmaceutical compound that is an inhibitor of fibrosis, such as, for example, compounds disclosed in U.S. Pat. No. 6,331,298.

The support may also be incorporated with at least one pharmaceutical compound that is capable of enhancing angiogenesis, such as, for example, compounds disclosed in U.S. Published Application 2004/0220393 and U.S. Published Application 2004/0209901.

The support may also be incorporated with at least one pharmaceutical compound that is an immunosuppressive compound, such as, for example, compounds disclosed in U.S. Published Application 2004/0171623.

The present invention is further illustrated, but not limited by, the following examples.

EXAMPLES

Example 1

Passage and Maintenance of hESC as Cell Clusters

The human embryonic stem cell lines H1 and H9 were maintained on mitomycin C inactivated primary mouse embryonic fibroblasts (MEF). The hES cells were switched from MEF feeders to MATRIGEL™ over repeated passages.

MATRIGEL™ coating of tissue culture dishes: Growth Factor Reduced MATRIGEL™ (Becton-Dickinson, Bedford, Mass.) was thawed at 4° C. and then diluted 1:30 in cold DMEM/F12 (Invitrogen, Carlsbad, Calif.). Volumes sufficient to cover were added to each 6 cm dish (2 ml) or each well of a 6 well plate (1 ml), and incubated 1 hr at room temp. Plates were used within a few hours or stored at 4° C. up to two weeks.

Human embryonic stem cell culture: Undifferentiated human embryonic stem cell colonies (H9 and H1) were harvested from feeder layers by incubation in 1 mg/ml collagenase IV (Sigma-Aldrich, St. Louis, Mo.) in DMEM/F12 for 10 minutes, followed by scraping with a pipet. Cell clumps were pelleted by centrifugation at 1000 rpm for four minutes and the pellet dispersed gently with a 2 ml pipet to break colonies into small clusters of cells. These cell clusters were seeded onto MATRIGEL™-coated dishes in MEF-CM supplemented with bFGF (8 ng/ml; R&D Systems, Minneapolis, Minn.), 50-150 colonies per 6 cm dish in 5 ml growth medium. Medium was changed daily. Colonies on MATRIGEL™ in MEF-CM became large and were passed when they occupied 70-80% of the surface area, approximately every 3-4 days. The hES cells in the colonies had a high nucleus to cytoplasm ratio and had prominent nucleoli, similar to hES cells maintained on feeders (FIG. 1). Differentiated cells represented less than 5% of total cells in culture.

For routine passage of cells in MEF-CM on MATRIGEL™, cells were incubated in 1 mg/ml collagenase IV in DMEM/F12 for up to 60 minutes and removed from the dishes by forceful streams of DMEM/F12 with scraping. Cells were pelleted, dispersed, and seeded at a 1:3 or 1:4 ratio.

Example 2

Passage of Human Embryonic Stem Cells as Single Cells: Evaluation of Enzymes

To facilitate the ease of handling hES cells, passaging techniques may use other enzymatic solutions which need a shorter incubation time and do not include a scraping step. Additionally, passaging cells as cell clusters with collagenase does not allow for numeric quantification of the cells that are seeded. Many enzymatic solutions are available to release single cells in one rapid step. A fast acting enzyme that causes minimal cell damage and does not impede cell attachment or cell growth was identified by the following experiment.

Human embryonic stem cells H9p33 cells grown in clusters in a 6 well dish were incubated with the following enzymes; TrypLE™Express (stable trypsin-like enzyme (Invitrogen (Carlsbad, CA)), TrypLE™Select (animal origin-free trypsin-like enzyme (Invitrogen (Carlsbad, CA)), trypsin/EDTA(0.05%), or trypsin (0.25%), for two minutes at 36° C. All enzymes released the cells within two minutes except trypsin. Release with trypsin was achieved after five minutes at 36° C. Cells were reseeded at 200,000 cells/well into a 6 well plate coated with MATRIGEL™ and allowed to expand for three days. Human embryonic stem cells were also passed as clusters with collagenase (30 minute incubation) and reseeded at a 1:5 dilution on MATRIGELT™-coated wells, similar to the counted TrypLE™Express cells. After three days, the hESC were released by a five minute incubation with TrypLE™Express. Cells were incubated with 0.01% trypan blue and then counted (Table I). Cell viability immediately after release was greater than 98% for all enzymes tested. Passage of human embryonic stem cells with collagenase is the standard passaging method. After three days culture, both TrypLE™Select and TrypLE™Express yielded recovered cell counts similar to collagenase. Trypsin/EDTA and trypsin were significantly less effective at maintaining cell attachment/growth. TrypLE™Select and TrypLE™Express were the best enzymes evaluated and were further tested in a time course experiment, Example 3.

Example 3

Passage of Human Embryonic Stem Cells as Single Cells: Optimization of Enzyme Exposure Time TrypLE™ Select and TrypLE™ Express proved optimal of all enzymes tested. To determine the ideal incubation time for these enzymes with hES cells, TrypLE™ Select and TrypLE™ Express were incubated with H9p34 hESC clusters for two minutes or 10 minutes at 37° C. Cells were removed from the well, counted, and pelleted by centrifugation. Aliquots of 200,000 cells/well were seeded into a 6 well plate. Cells were grown for three days followed by release with TrypLE™ Express and counting in the presence of 0.01% trypan blue.

Cell viability was greater than 98% for both enzymes for both incubation times. Table II indicates the number of recovered cells/well 36 hrs after seeding. Cells passed with TrypLE™Express reached the initial seeding density after three days. This indicates that the majority of cells do not reattach after seeding; however, the cells that do attach are able to proliferate and expand. Assuming that the cells expand at the same rate once attached, these data demonstrate that a treatment of two minutes with TrypLE™Express results in the best attachment rate. TrypLE™Express treatments for two minutes were then used for making single cells in all subsequent experiments.

Example 4

Differentiation of Human Embryonic Stem Cells Single Cells and Cell Clusters to Definitive Endoderm Embryonic stem cells can differentiate into multiple cell lineages. Human ES cells passaged as single cells offer a significant improvement to aid in cell input quantification and ease of handling. The ability of these single hES cells to differentiate was determined.

Seeding of cell clusters and single cells: A 6 cm plate of H9 or H1 cell clusters on reduced growth factor MATRIGEL™ was incubated with 2 ml collagenase (1 mg/ml) in DMEM:F12 for up to 60 minutes at 37° C. The cells were removed by pipetting and scraping and centrifuged for 4 minutes at 900 rpm. The cell clusters were then seeded into a 6 well plate coated with 1:15 or 1:30 reduced growth factor MATRIGEL™. This passaging method resulted in seeding cell clusters (cc). Alternatively, a 6 cm plate of H9 or H1 cell clusters on reduced growth factor MATRIGEL™ were incubated with TrypLE™ Express (2 ml) for 5 minutes at 37° C. and dispersed by pipetting. Following centrifugation at 900 rpm for 4 minutes, the cells were then seeded into a 6 well plated coated with 1:10 reduced growth factor MATRIGEL™ and named single cells (sc).

Definitive Endoderm differentiation: H9 and H1 sc and cc cultures at approximately 60 to 70% confluency were exposed to DMEM:F12 medium supplemented with 0.5% FBS, 10 ng/ml Wnt3a (R&D Systems) and 100 ng/ml Activin A (AA; R&D Systems) for two days, followed by treatment with DMEM/F12 medium supplemented with 2% FBS and 100 ng/ml activin A for an additional three days.

Figure 2:
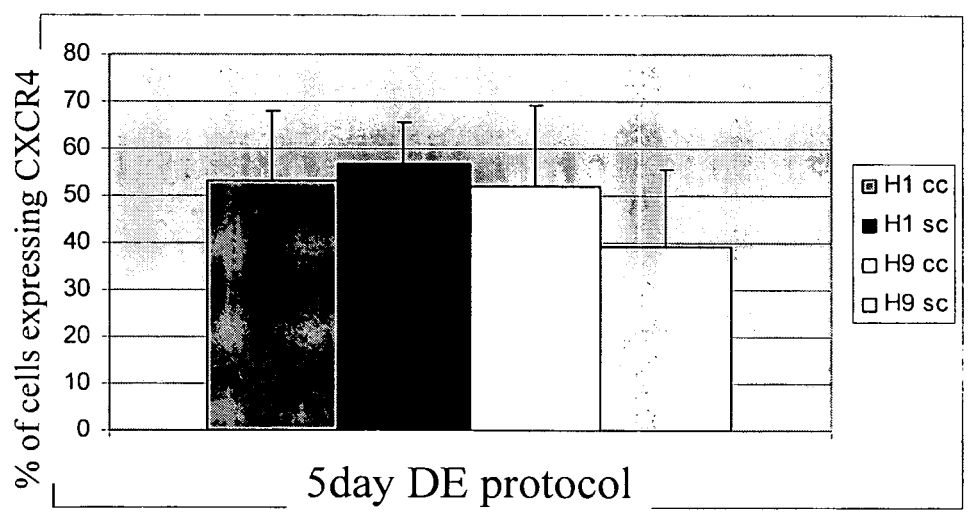
FIG. 2: Percentage of cells expressing CXCR4 after differentiation treatment to derive definitive endoderm. Dark grey: An average of six DE differentiation experiments with H1 cell clusters (H1 cc) between passages 45 and 55. Black: An average of two DE differentiation experiments with H1 single cells (H1 sc) at passage 47 and 54. White: An average of five DE differentiation experiments with H9 cell clusters (H9 cc) between passages 37 and 55. Light grey: An average of three DE differentiation experiments with H9 single cells (H9 sc) between passages 36 and 48. Error bars represent the standard deviation of replicate experiments.

The cultures were analyzed by FACS for CXCR4, CD99, and CD9 expression and by real time PCR for SOX-17, SOX-7, Alpha-fetal protein (AFP), CXCR4, Brychyury (Bry), goosecoid (GSC), HNF-3 beta, and GATA4. AFP and SOX-7 are regarded as visceral endoderm markers, while GATA4, HNF-3 beta and SOX-17 represent definite endoderm markers, and GSC, Bry, and CXCR4 represent markers of primitive streak. Single cells differentiated to DE to a similar extent as cell clusters as observed through the percentage of resulting CXCR4 positive cells (FIG. 2).

Example 5

Differentiation of hES Single Cells and Cell Clusters to Pancreatic Endoderm

Further differentiation, following a protocol published by Novocell (D'Amour, KE et al., Nature Biotechnology (2006), 24(11), 1392-1401) with modifications, was also tested to determine the differentiation capacity of the hES single cells. The cells were further differentiated into pancreatic endoderm following the DE protocol described in Example 4.

Figure 3:
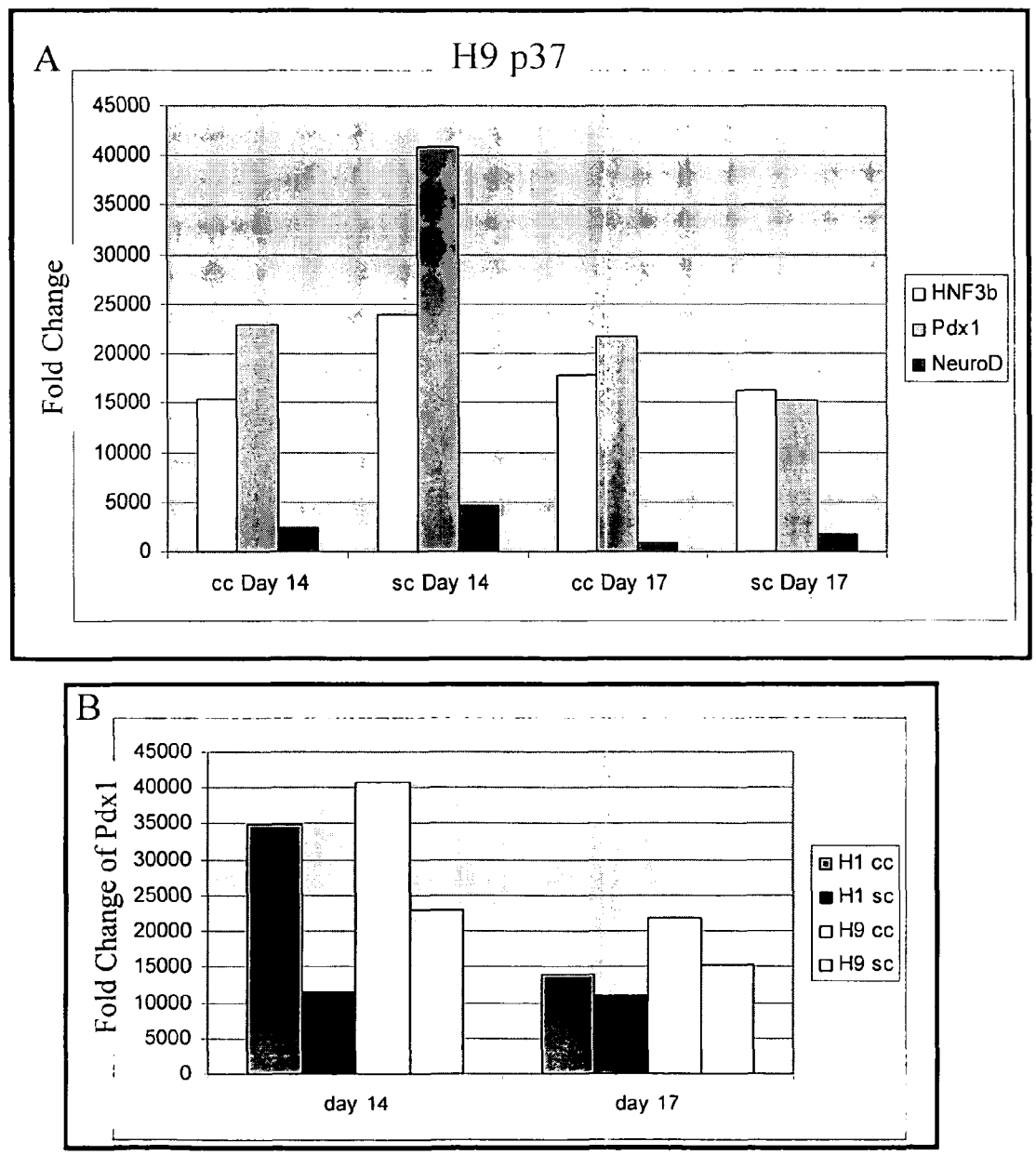
FIG. 3: Analysis of gene expression by real-time PCR after exposure to 14 or 17 days of the pancreatic endocrine differentiation protocol. A. H9 single cells and cell clusters at passage 37 were analyzed. B. Continuation of H1 p47 and H9 p37 cell clusters and single cells to the pancreatic endoderm stage. Pdx1 expression after days 14 and 17. Gene expression for the indicated markers for untreated cells was set to a value of one for each data set.

Pancreatic Endoderm differentiation: One of the H9 (p37) DE experiments, using both cell clusters and single cells from example 4, was further differentiated to pancreatic endoderm. After completion of the definitive endoderm protocol, the cells were incubated for 3 days with FGF10 (50 ng/ml; R&D Systems), the sonic hedgehog inhibitor, KAAD cyclopamine (2.5 uM; Sigma-Aldrich) and 2% FBS in DMEM:F12 medium. Following, cells were incubated an additional three days with FGF10 (50 ng/ml), KAAD cyclopamine (2.5 uM), Retinoic Acid (1 uM; Sigma-Aldrich) and 1% B27 (Invitrogen) in DMEM-low glucose. Following, cells were incubated an additional three days in Exendin 4 (50 ng/ml; Sigma-Aldrich), DAPT (1 uM; Calbiochem), and 1% B27 in DMEM-low glucose. RNA samples were taken from one well of a 6 well plate for each cell type and then analyzed by real-time PCR at this step for pancreatic markers Pdx1, Nkx6.1, Nkx2.2, Pax4, NeuroD, HNF3b, Ptf1a, Insulin and AFP. Differentiation was continued for three days with CMRL medium (Invitrogen) containing 50 ng/ml, HGF, IGF (R&D Systems), and Exendin 4 (50 ng/ml), and 1% B27. Evaluation of the same pancreatic endoderm markers was repeated at this stage. RNA samples from untreated hES cells of the same line were subjected to real-time PCR in parallel to treated samples. Treated samples were normalized to untreated controls set to a fold change of one. Pdx1 expression was monitored and compared between single cells and cell clusters. Induction of pancreatic endoderm marker expression was equivalent between the single cells and the cell clusters (FIG. 3). Therefore, the hES single cells have a similar inherent capacity to differentiate as hES cell clusters.

Example 6

Passage of hES Cells as Single Cells

Passage of hES cells as single cells would aid in the ability to scale-up cultures and facilitate a manufacturing process.

Figure 4:
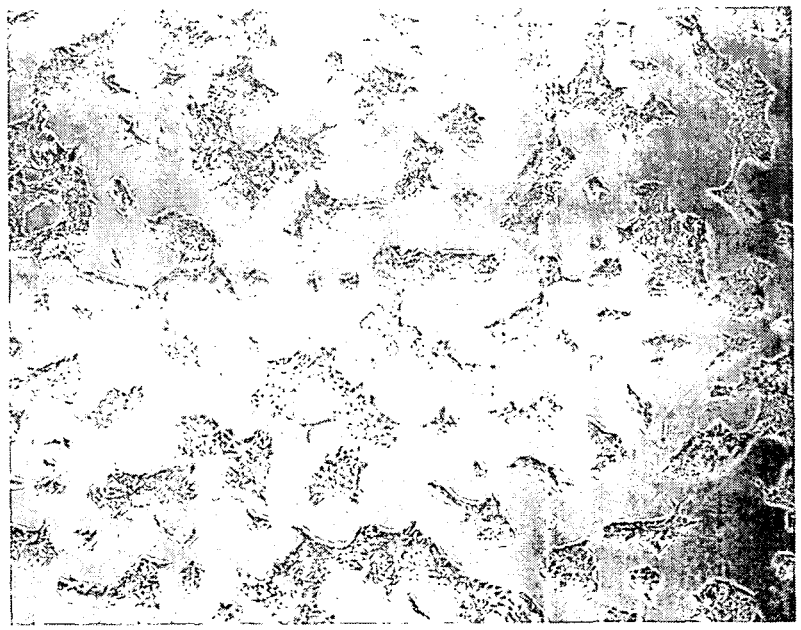
FIG. 4: An image is shown at 4× enlargement of H9scp22 human ES single cells grown on 1:30 reduced growth factor MATRIGEL™ in MEF-conditioned medium.

Description of single cell generation and passage: H9 cells were grown as clusters on MATRIGEL™ as described above. At passage 38, a 6 cm plate of H9 cells was incubated with 2 ml TrypLE™ Express for 5 minutes at 37° C. The cells were resuspended in DMEM:F12 and centrifuged for 4 minutes at 900 rpm. The cells were reseeded at a 1:4 ratio onto 1:30 growth factor reduced MATRIGEL™ coated plates. After approximately five passages, the cells were counted before reseeding and plated at a density of 14,000 cells/cm². Passage and reseeding at this density continued at intervals of every four days. The cells retained a compact structure as they grew out of single cells but never formed tight clusters (compare FIG. 1 and FIG. 4).

Example 7

Analysis of hES Single Cell Pluripotency

Maintenance of hES cell pluripotency is necessary with any passaging technique. Therefore, the single cells were evaluated for pluripotency after multiple passages with TrypLE™ Express.

Figure 5:
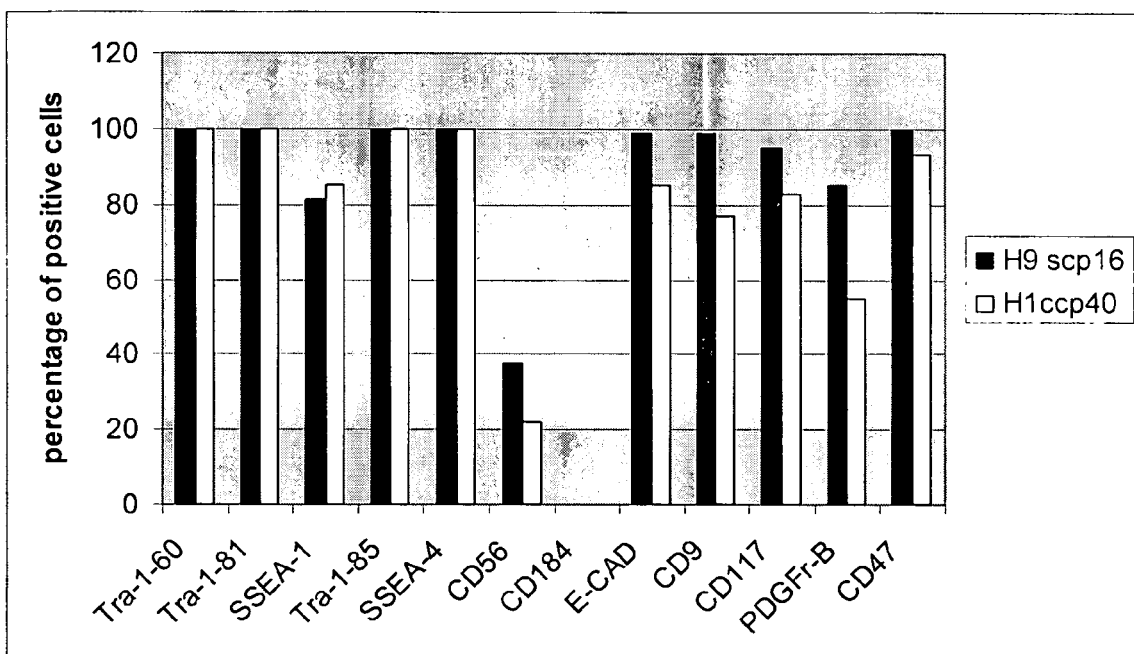
FIG. 5: Evaluation by FACS for pluripotency marker expression of hES cells. The percentage of cells positive for indicated markers is listed on the X-axis.

FACS pluripotency analysis: H9 single cells were cultured 38 passages as clusters followed by 16 passages as single cells including one cryopreservation freeze-thaw. The cells were then analyzed by FACS for the expression of pluripotency markers. Adherent cells were removed from culture plates using a 5 minute incubation with TrypLE™Express solution. Released cells were resuspended in DMEM:F12 medium and recovered by centrifugation, followed by washing and resuspending in a staining buffer consisting of 2% BSA (Sigma-Aldrich, St. Louis, MO), 0.05% sodium azide in PBS. As appropriate, the cells were Fc-receptor blocked for 15 minutes using a 0.1% gamma globulin (Sigma) solution. Aliquots (approximately 105 cells) were incubated with either phycoerythirin (PE) or allophycocyanin (APC) conjugated monoclonal antibodies (5 µl antibody per 106 cells), as indicated in Table IIIA, or with an unconjugated primary antibody. Controls included appropriate isotype matched antibodies, unstained cells, and cells stained only with secondary conjugated antibody. All incubations with antibodies were performed for 30 minutes at 4° C. after which the cells were washed with the staining buffer. Samples that were stained with unconjugated primary antibodies were incubated for an additional 30 minutes at 4° C. with secondary conjugated PE or APC labeled antibodies. See Table IIIB for a list of secondary antibodies used. Washed cells were pelleted and resuspended in the staining buffer, and the cell surface molecules were identified using a FACS Array (BD Biosciences) instrument, collecting at least 10,000 events. hESC collagenase passaged H1p40 and H9scp16 have equivalent pluripotency protein expression profiles (FIG. 5).

Example 8

Analysis of Human Embryonic Stem Cells Single Cell Karyotype Stability

Figure 6:
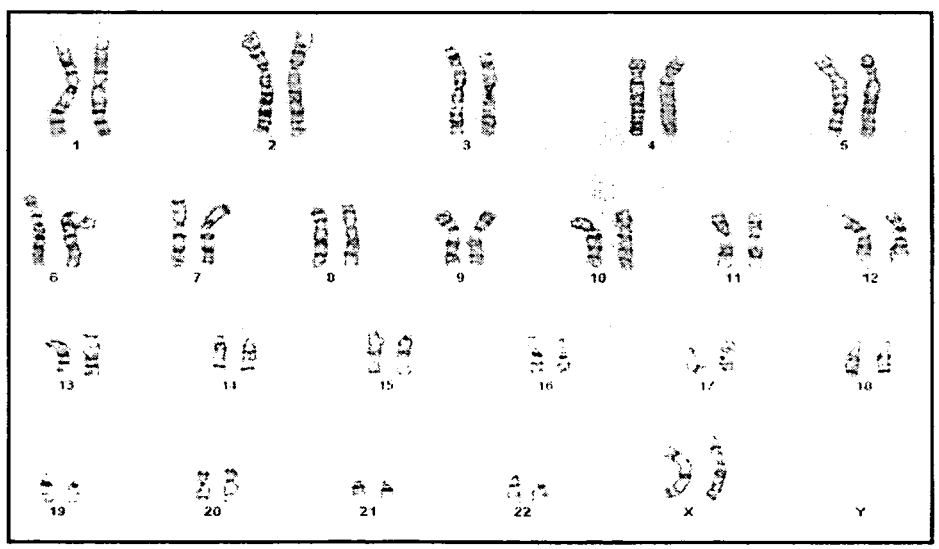
FIG. 6: Chromosomal spread of H9 hES single cells at passaged 38 times as clusters followed by 20 passages as single cells

The karyotype of hES single cells should remain stable over multiple passages. H9 single cells were cultured 38 passages as clusters followed by multiple passages as single cells. The karyotype of H9 cells was determined by standard G-banding karyotype analysis (Cell Line Genetics, Madison, Wis.). A total of 20 G-banded cells were evaluated and 200 interphase nuclei were analyzed by FISH (fluorescence in situ hybridization). No chromosome aberrations were found in the cells analyzed. Cytogenetic analysis showed that the cells had a normal number of autosomes and a modal chromosome number of 46. Karyotyping of H9 single cells was conducted at passage 13 and passage 20. Passage 20 cells had undergone one cryopreservation freeze-thaw event. Passage 13 and 20 cells were karyotypically normal (FIG. 6).

Example 9

Differentiation of hES Single Cells and hES Cell Clusters to Definitive Endoderm For ultimate utility, hES cells passaged as single cells must retain their differentiation potential. Single cells were subjected to the definitive endoderm protocol as follows. H9 cells after multiple passages with TrypLE™ Express (sc-p), were released with TrypLE™ Express (sc) from passed single cells (passage 6 and 21) onto MATRIGEL™ (1:10 dilution) for differentiation. H9 sc, at approximately 60 to 70% confluent monolayers, were exposed to DMEM:F12 medium supplemented with 0.5% FBS, 10 ng/ml Wnt3a and 100 ng/ml activin A for two days, followed by treatment with DMEM/F12 medium supplemented with 2% FBS and 100 ng/ml Activin A for an additional three days.

Figure 7:
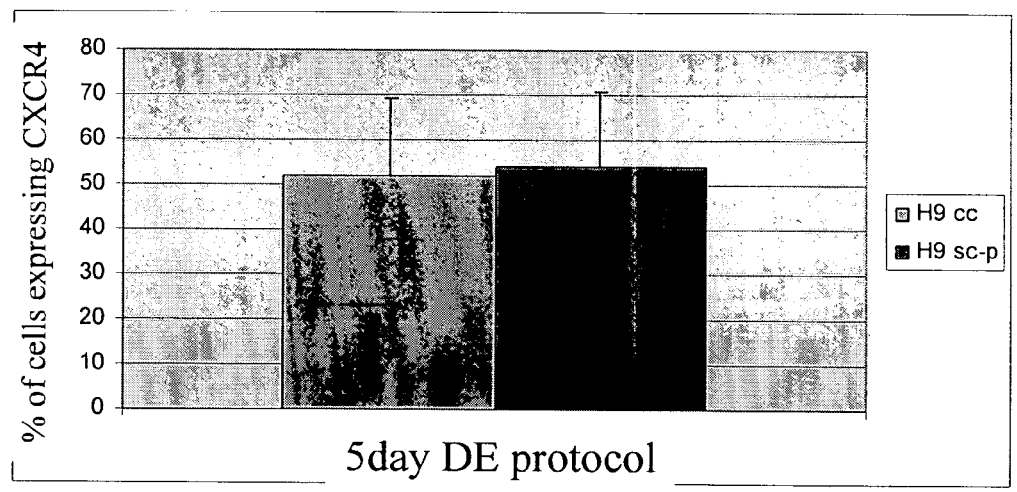
FIG. 7: Comparison of H9 single cells and cell clusters during definitive endoderm differentiation. The percentage of cells positive for CXCR4 is shown after the cells are exposed to the definitive endoderm differentiation protocol. N=2 for H9sc-p and N=5 for H9 cc. Error bars represent standard deviation of the mean for replicate experiments.

At day 5, the cells were analyzed by FACS for CXCR4, CD99, and CD9 expression and by real time PCR for SOX-17, SOX-7, Alpha-fetal protein (AFP), CXCR4, Brychyury (Bry), goosecoid (GSC), HNF-3 beta, and GATA4. AFP and SOX-7 are regarded as visceral endoderm markers, while GATA4, HNF-3 beta and SOX-17 represent definite endoderm markers, and GSC, Bry, and CXCR4 represent markers of primitive streak. Single cells passed multiple times (passage 6 and 21) retain their ability to differentiate into DE, similar to cell clusters (passage 36-55) (FIG. 7).

Example 10

Differentiation of hES Single Cells to Pancreatic Endoderm

Figure 8:
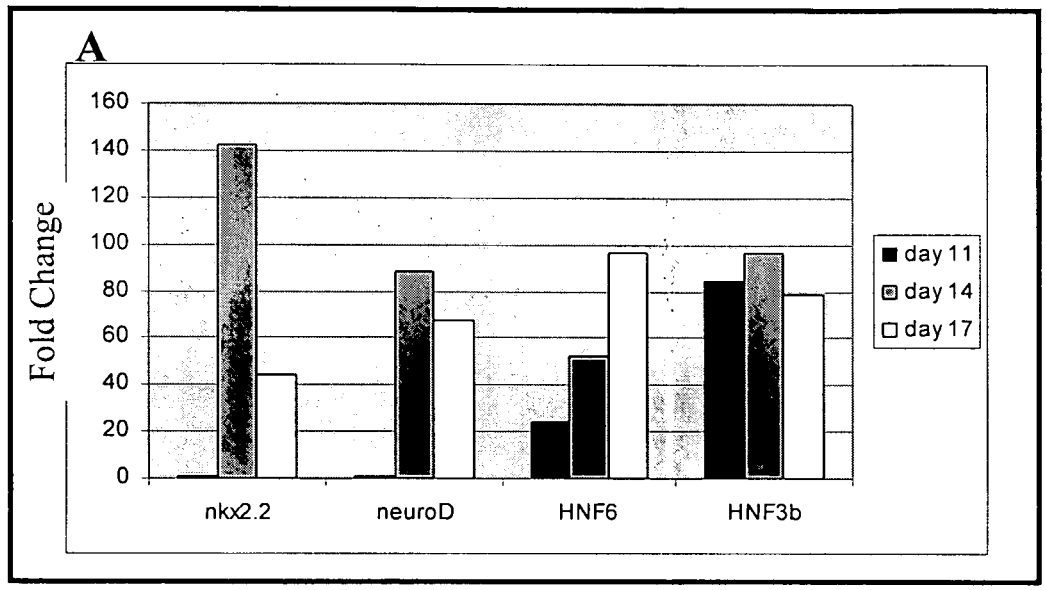
FIG. 8: Increase in pancreatic endoderm makers after H9 single cells (passage 22) are differentiated. Analysis of gene expression by real-time PCR is shown after 11, 14 or 17 days of pancreatic endocrine differentiation. Values for days 14 and 17 are an average of two wells from a 6 well plate
Figure 8:
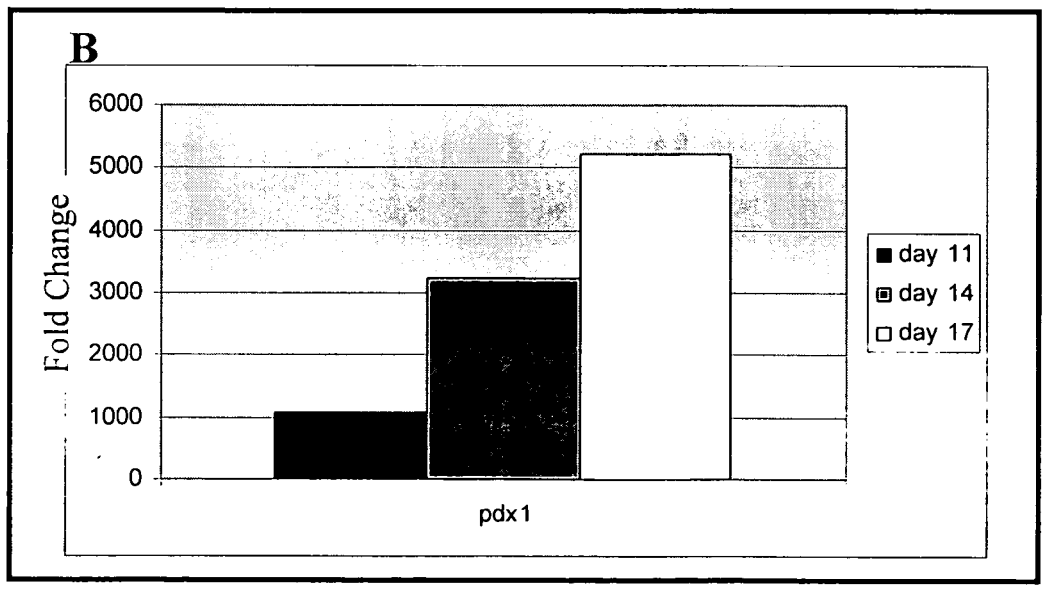

Cells were further differentiated into pancreatic endoderm adhering to the following steps; three day incubation with FGF10 (50 ng/ml), the sonic hedgehog inhibitor, KAAD cyclopamine (2.5 uM), and 2% FBS in DMEM:F12 medium, followed by three days with FGF10 (50 ng/ml), KAAD cyclopamine (2.5 uM), Retinoic Acid (1 uM) and 1% B27 in DMEM-low glucose. Evaluation of the cells was performed at day 11. Some cultures continued treatment for three days in Exendin 4 (50 ng/ml), DAPT (1 uM), and 1% B27 in DMEM-low glucose. At day 14, samples were analyzed for pancreatic markers Pdx1, Nkx6.1, Nkx2.2, Pax4, NeuroD, HNF3b, Ptf1a, Insulin and AFP by real-time PCR. Some cultures continued differentiation for an additional three days with CMRL medium containing 50 ng/ml, HGF, IGF, and Exendin 4, and 1% B27. Evaluation of the same pancreatic endoderm markers was repeated at the end of day 17. Pancreatic endoderm markers, Nkx2.2, NeuroD, HNF6, HNF3b, were predominantly expressed at the end of days 14 and 17. Pdx1 expression increased stepwise at each stage of treatment (FIG. 8).

Example 11

Differentiating hES Single Cells on MEF Feeders

Figure 9:
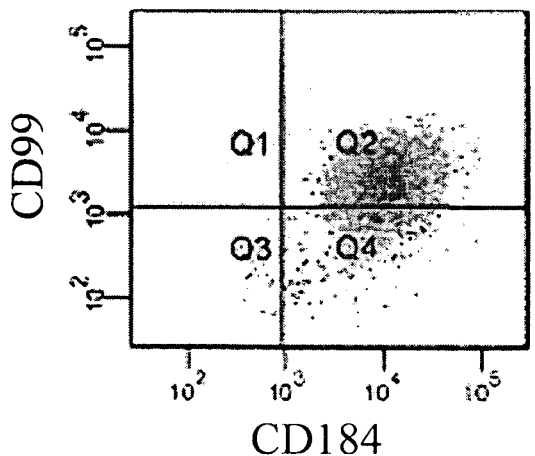
FIG. 9: hES single cells can be differentiated on MEFs. FACS results from H1scp4 cells grown on MEF feeders and differentiated to definitive endoderm. The definitive endoderm marker CXCR4 (CD184) is expressed in 89% of the cells versus 0% in undifferentiated cells (see FIG. 5).
Figure 9:
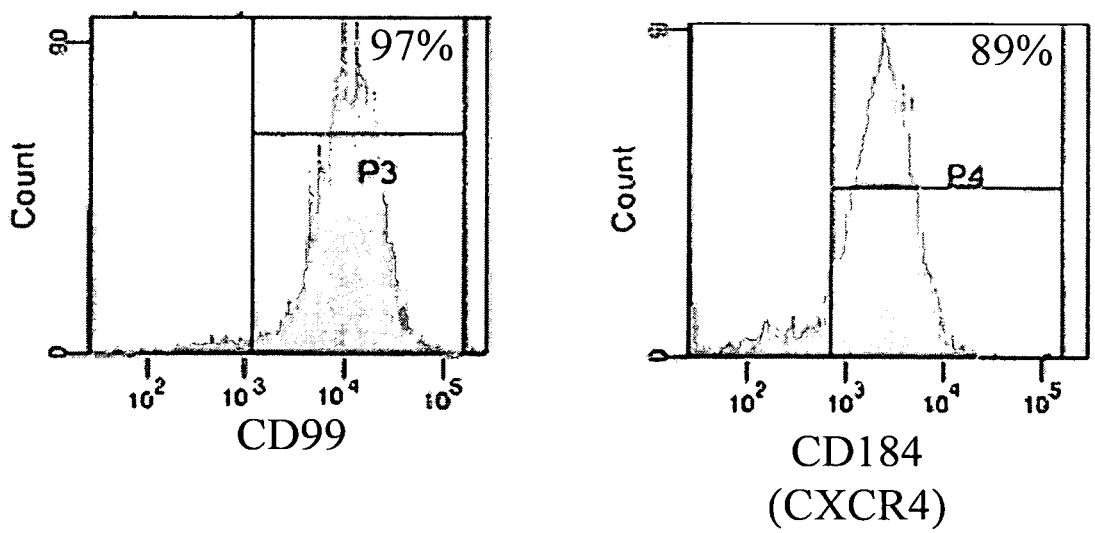

To achieve optimal differentiation of hES cells to pancreatic endoderm, the definitive endoderm population must be maximal. Currently, growing hES on MEF feeders results in the highest achievable levels of definitive endoderm and pancreatic endoderm. To determine if the hES single cells are able to achieve this end, H1scp4 were seeded onto MEF feeders at 14,000 cells/cm$^2$. The cells were grown in ES cell medium containing 20% Knock-out Serum Replacement (Invitrogen), 1× non-essential Amino Acids (Invitrogen), 8 ng/ml bFGF, 1 mM L-glutamine and 1 mM 2-mercaptoethanol solution in DMEM-F12. After 7 days cells were 60-70% confluent, and the definitive endoderm protocol was applied to the cells. Specifically, two days of 100 ng/ml Activin A, 10 ng/ml Wnt3a and 0.5% FBS in DMEM:F12 medium was added, 100 ul per well followed by three day treatment with 100 ng/ml Activin A and 2% FBS in DMEM:F12 medium. The cells were then removed with TrypLE™ Express and analyzed by FACS for CXCR4, CD99 and CD9 expression (FIG. 9). Greater than 90% of the cells expressed CXCR4 and CD99. Less than 8% of the cells expressed CD9, as expected. Seeding single H1 cells on MEF feeders improves definitive endoderm differentiation as determined by CXCR4 positive cell numbers.

Example 12

Differentiating hES Single Cells in 96 Well Plates

Figure 10:
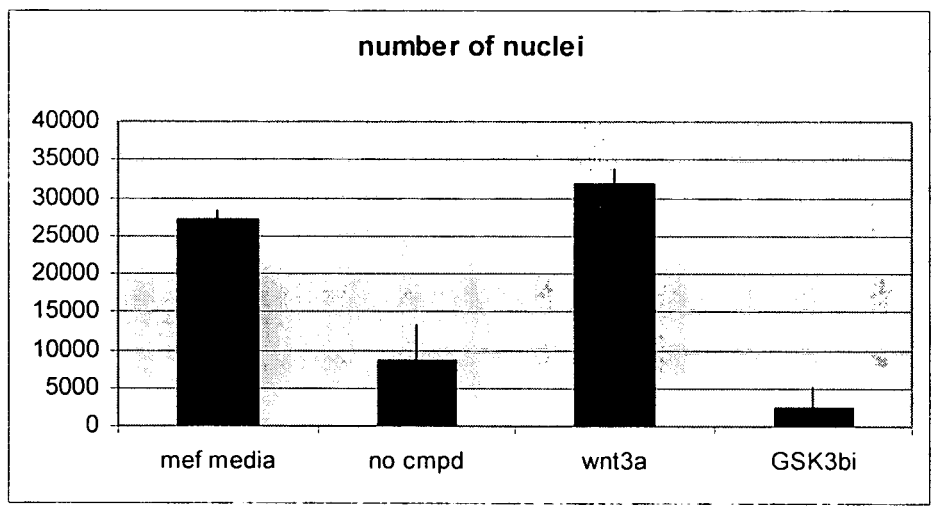
FIG. 10: hES single cells (H9scp18) can be differentiated in 96 well format to definitive endoderm. Immunofluorescence data for Sox17 positive detection is shown. Eight wells were treated with MEF-conditioned medium for the duration of the experiment: MEF media. Eight wells were treated with the basal differentiation medium without components: no compd. Replicate data sets of eight wells were averaged for each data bar. A total of 40 wells were each treated with Wnt3a or Gsk3b inhibitor and averaged for each data set. The error bars represent the standard deviation for each replicate set.
Figure 10:
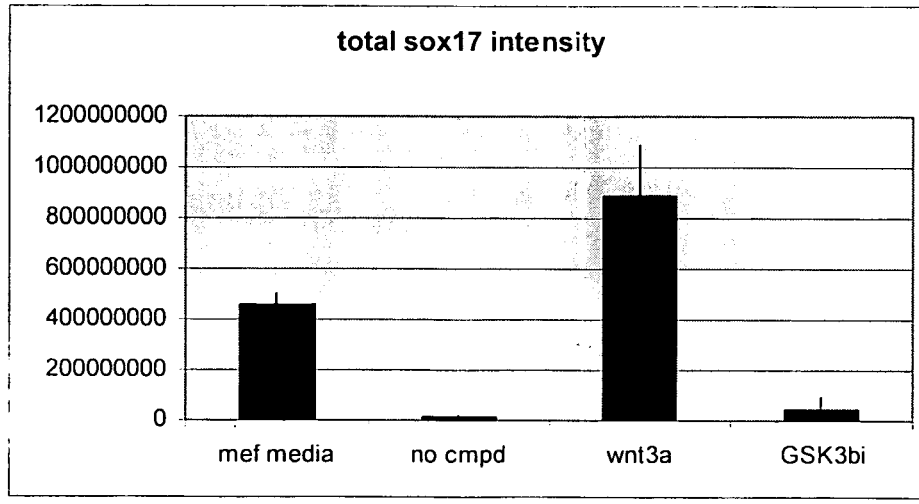

One common difficulty with passage of hES cells as clusters is that they are difficult to quantify and do not grow at even rates. Single cells have the advantage that they can grow to a confluent monolayer and can be counted before passage to ensure equal seeding for experimental purposes. These attributes are a prerequisite for successful screening validation.

hES H9scp18 were seeded into Packard View 96-well plates (Perkin-Elmer) coated with 1:30 growth factor reduced MATRIGEL™ at a density of 14,000 cells/cm$^2$. The cells were grown for three to four days in MEF conditioned medium and then treated using a DE differentiation protocol. A subset of 40 wells was treated with a standard protocol (10 ng/ml Wnt3a, 100 ng/ml Activin A, and 0.5% FBS in DMEM:F12 for two days). A second subset of 40 wells was treated with the GSK3b inhibitor IX (100 nM; EMD Chemicals, La Jolla, Calif.) instead of Wnt3a. This was followed by treatment for both subsets for three days with 100 ng/ml Activin A and 2% FBS in DMEM:F12. At the end of culture, cells were fixed with 4% paraformaldehyde at room temperature for 20 minutes, washed three times with PBS, and stored in 100 ul PBS overnight. Cells were permeabilized with 0.5% Triton X-100 (Sigma-Aldrich), either at room temperature for 20 minutes or at 4° C. for five minutes, then washed three times with PBS and blocked with 4% chicken serum (Invitrogen-Gibco, Carlesbad, Calif.) in PBS for 30 minutes at room temperature. Primary antibodies (goat-anti-hSox17 (R&D Systems) were diluted and added in 4% chicken serum at 1:100 dilution for 1 hr at room temperature. The secondary antibody, Alexa Fluor 488 chicken-anti goat IgG (Invitrogen-Molecular Probes, Carlesbad, Calif.) was diluted 1:200 in PBS and added to the cells after washing 3 times with PBS. To counterstain the nuclei, 5 µM Draq5 (Alexis Platform, Laufelfingen, Switzerland) was added to the cells for 5 minutes at room temperature. Cells were washed once with PBS and left in 100 µl/well PBS for imaging to determine the number of differentiated DE cells. The plate was read on an IN Cell 1000 Analyzer (GE Healthcare; Piscataway, N.J.) for well-to-well quantification of cell number and Sox 17 staining. Treatment with Wnt3a resulted in the highest number of cell nuclei per well with little variability between wells (FIG. 10). Treatment with the Gsk3β inhibitor showed poor cell viability. Clearly, Wnt3a treatment allows single ES cells to form DE in a robust and reproducible manner in a 96 well format.

Example 13

Screening Assays with hES Single Cells

Figure 11:
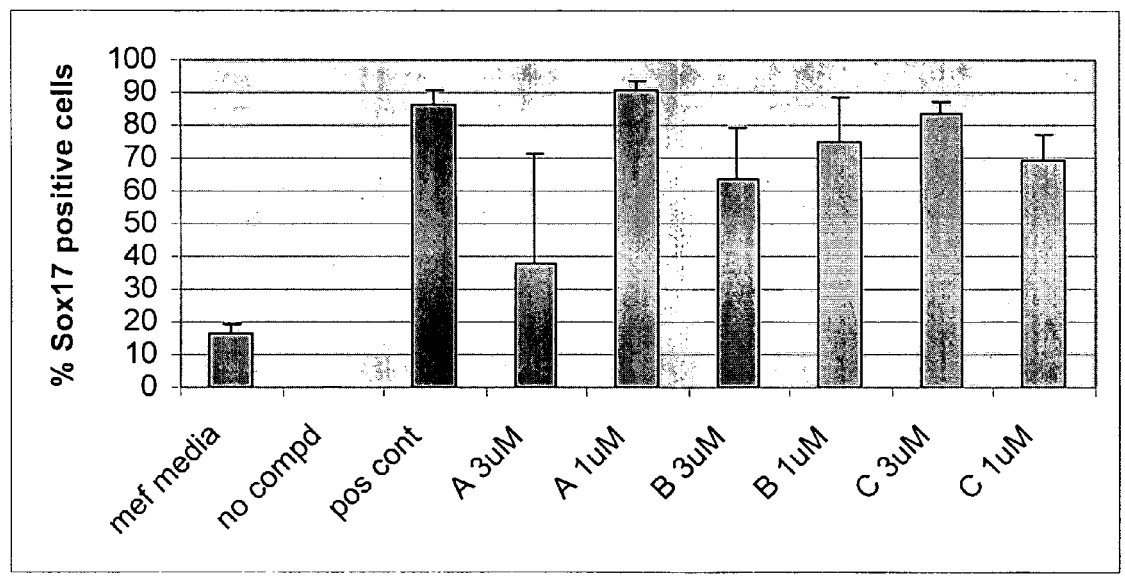
FIG. 11: Pharmacophore screening with hES single cells, (H9scp19). A total of 13 experimental small molecule compounds were tested for their ability to substitute for Wnt3a in the definitive endoderm differentiation protocol. Three effective compounds are shown. The data sets represent an average of Sox17 positive cells in two or more wells. Cells treated with MEF-conditioned medium or basal medium were used as negative controls

After demonstrating that single cells are amenable to seeding and differentiation in 96 well format, sensitivity to treatment with novel compounds was determined. hES H9scp19 were seeded into 96 well plates coated with 1:30 growth factor reduced MATRIGEL™ at a density of 14,000 cells/cm$^2$. The cells were grown for 3-4 days in MEF conditioned medium and then processed in a DE differentiation experiment. A total of 13 novel compounds were tested in triplicate at a concentration of 1 or 3 µM, substituting the small molecule inhibitor for Wnt3a in the DE differentiation protocol. Wells containing Wnt3a (10 ng/ml) or Gsk3b inhibitor IX (100 nM) were used as positive controls. All differentiation wells were treated with a single compound plus 100 ng/ml Activin A and 0.5% FBS in DMEM:F12 for two days followed by two days in the absence of compound with 100 ng/ml Activin A and 2% FBS in DMEM:F12. At the end of the protocol, the cells were fixed, permeabilized, blocked, and stained as described in example 11 above to determine Sox 17 expression and nuclei. The plate was then read on an IN Cell 1000 Analyzer. This screen indicated that H9scp21 responded to 3 of 13 compounds in a manner similar to Wnt3a in the DE differentiation protocol (FIG. 11). Compound A was effective at the 1 µM lower dose whereas compounds B and C were effective at both 1 and 3 µM. In the effective treatment range (greater than 60% Sox17 positive cells), the standard deviation between wells was small. Thus, single cells are consistent in their ability to identify novel compounds through screening techniques.

Example 14

Expansion of Single hES Cells in Roller Bottles

To facilitate scale up for manufacturing goals, hES cells need to be easily expanded into large quantities. Currently, collagenase treatment to passage hES cells is not amenable to scale-up in roller bottles or shaker flasks. HES cells repeatedly expanded and grown as single cells have the ability to adhere evenly to different surfaces. In this example, roller bottles were tested as potential scale-up vessels. H9scp19 were seeded at 14,000cells/cm$^2$ into a 480cm$^2$ roller bottle (6.7×10$^6$ cells; Corning, Acton, Mass.) coated with 1:30 reduced growth factor MATRIGEL™. Volumes of 100ml of MEF conditioned medium per bottle were used to maintain the cells, changed every two days. The bottles were set at 20 rev/hr for 24 hrs and increased to 60 rev/hr for the remaining time. The cells adhered evenly to the roller bottle and visibly expanded over the four day evaluation period. The cells were removed using TrypLE™Express and counted. Recovery counts indicated 13×10$^6$ cells per bottle were obtained, indicating a minimal doubling of the cells occurred compared to the original seeding. It is estimated that less than half of the initially seeded cells attached to the roller bottle, suggesting that a larger actual cell expansion occurred in the roller bottles. This demonstrates that hES cells passed as single cells can be expanded in an automated roller bottle system. Further experiments to determine the expansion rate along with maintenance of pluripotency will be conducted.

Example 15

Transfection of Single hES Cells

Introducing DNA into cells to make transgenic cell types is a useful feature. The DNA may contain an expression vector or a reporter gene to facilitate differentiation or to allow selection of the cells. hES cells have proven difficult to transfect in clusters. However, hES single cells may be more amenable to transfection techniques.

Figure 12:
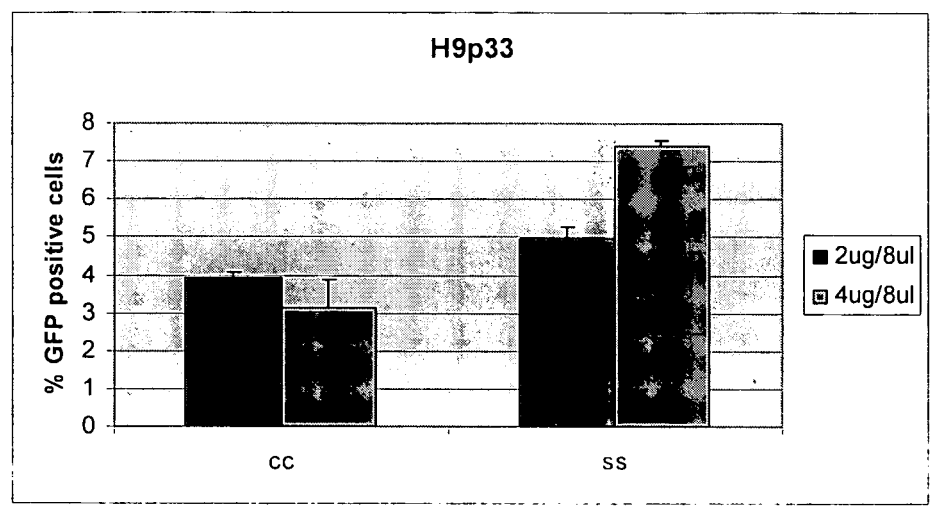
FIG. 12: Evaluation of transfection efficiency between H9p33 hES cell clusters and single cells. CMV-GFP was transfected into cells using eight μl Lipofectamine 2000 (Invitrogen, Carlesbad, Calif.) and four or eight μg DNA, black and grey bars respectively.

H9p33 cells were passed with TrypLE™ Express and seeded at 20,000 cells/cm$^2$ onto a 1:30 reduced growth factor MATRIGEL™ coated plate. H9p33 cells were passed with collagenase and seeded from one 6 cm plate into one well of a 6well plate coated with 1:30 reduced growth factor MATRIGEL™. After 3 days, the cells were transfected with CMV-GFP, where GFP is expressed in every cell under the CMV viral promoter. Specifically, 2 or 4 µg of DNA was diluted in 250 µl Opti-MEM medium and 8 µl of Lipofectamine 2000 (Invitrogen) into 250 µl Opti-MEM. The mixtures are combined after five minutes at room temperature. The combined reagents were incubated for 20 minutes at room temperature before adding to the cells cultured in two ml of MEF-conditioned media. The medium was replaced with MEF conditioned medium every 24 hours thereafter. After three days, the cells were fixed with 4% paraformaldehyde at room temperature for 20 minutes then washed two times with PBS and left in PBS at 4° C. overnight. To counterstain the nuclei, 5 µM Draq5 (Alexis Platform) was added to the cells for five minutes at room temperature. Cells were washed once with PBS and left in 1 ml/well PBS for imaging on the IN Cell 1000 Analyzer to determine transfection efficiency (FIG. 12). HES single cells show a two-fold improvement in transfection efficiency over hES clusters. Therefore, hES single cells have an improved transfection capacity and are easier to genetically modify. With optimization, perhaps using other transfection methods or regents, it may be possible to achieve a more dramatic improvement of single cell ES cell transfection.

Example 16

Conversion of hES Cell Clusters Cultured on a Feeder Cell Layer to Single hES Cells Cultured on an Extracellular Matrix Requires Removal of Feeder Cells The passage of mammalian cells with enzymes such as trypsin, recombinant trypsin (TrypLE™), or Accutase™ (invertebrate derived trypsin-like enzyme) is the current standard for cell culture of both primary and immortalized cell lines in research and manufacturing settings. These enzymes produce a homogenous single cell suspension of cells that can be counted, analyzed, manipulated and passaged in a reproducible manner amenable to plating in settings as diverse as a high throughput format 384 well plate or a multi-liter scaleable culture vessel.

Given the obvious advantages of single cell passage, there is considerable interest in developing a method pass human embryonic stem cells as single cells. However, current best practices with human embryonic stem cells require that the cells be passaged in clusters by either manual disruption or passage with an enzyme (collagenase or neutral protease) that maintains clusters of embryonic cells. Past research in this area has resulted in the derivation of cells that can be passaged as single cells onto feeders (Cellartis SCEDTM461 line), or derivation of single cells from collagenase passed clusters to single cells on MATRIGEL™ with Accutase™ (R. Bajpai et al., 2008).

Herein is an attempt to develop a single cell passage method to take hES cells directly from feeders to matrigel in a bulk passage method using either TrypLE™ or Accutase™. The results indicate that taking cluster style feeder based passage of hES cells directly to MATRIGEL™ using either TrypLE™ or Accutase™ bulk passage without an intermediate step of cluster based collagenase passage onto MATRIGEL™ is inefficient due to the appearance of a differentiated cell population and is therefore less likely to result in a homogenous and robust hES cell culture.

Results

In an effort to move to a feeder free culture of hES cells from a feeder based culture, H1 passage 37 hES cells that had been supported by a MEF feeder layer in hESC media and grown for 5 days on 10cm$^2$ wells of 6 well plates were passaged. The cells were passaged with either TrypLE™, Accutase™, or 1mg/ml of collagenase.

Before adding enzyme to the cells, the spent media was aspirated, 1 ml PBS (no Ca$^{2+}$, or Mg$^{2+}$) was added to each well, was aspirated again, and then 1ml of room temperature enzyme (collagenase, Accutase™, or TrypLE™) was added. Accutase™or TrypLE™were used at stock concentration after reaching room temperature. Collagenase was removed from −80° C. freezer, thawed, mixed with 9ml DMEM/F12, sterile filtered, and allowed to reach room temperature before use.

The cells were incubated in enzyme at 37° C. for 10 min. Accutase™ or TrypLE™ caused all the cells to completely lift from the dish after a 10-minute treatment. Collagenase did not lift cells after 10 minutes incubation, so the cells were scrapped with a 10 ml glass pipette after 10-minute incubation. One ml of 2% Probumin in DMEM-F12 was added to each well and the combined total volume in the well was transferred to a 50 ml sterile conical tube, making sure to lift and suspend as many cells as possible.

The cells were centrifuged for 5 minutes at 200×g followed by an additional wash with 2% Probumin and centrifugation for 5 minutes at 200×g. Cell were then resuspended in MEF conditioned media and plated at a 1 to 3.5 ratio onto MATRIGEL™ (1:30 dilution in DMEM) coated T25 flasks, and placed in a 37° C., 5% CO2, humidified incubator.

Cell number was calculated by counting with an Improved Neubauer hemocytomer. Cells that were lifted with Accutase™ had a density of 3.8 million cells/10 cm² well. Cells that were lifted with TrypLE™ had a density of 3.7 million cells/10 cm² well. Collagenase was not countable by hemocytometer due to colony style. Given a 1 to 3.5 split ratio, we plated the Accutase treated cells at a seeding density of 2.72 million cells/T25 flask or 108,000 cells/cm², the TrypLE™ treated cells at a seeding density 2.65 million cells/T25flask or 105,000 cells/cm². We assume that Collagenase treated wells were seeded at a similar density (105,000 to 108,000 cells/cm²), since there was no appreciable difference in hES density from well to well before enzyme treatment. An additional flask was plated with Collagenase lifted cells for counting purposes at the next passage.

Figure 13:
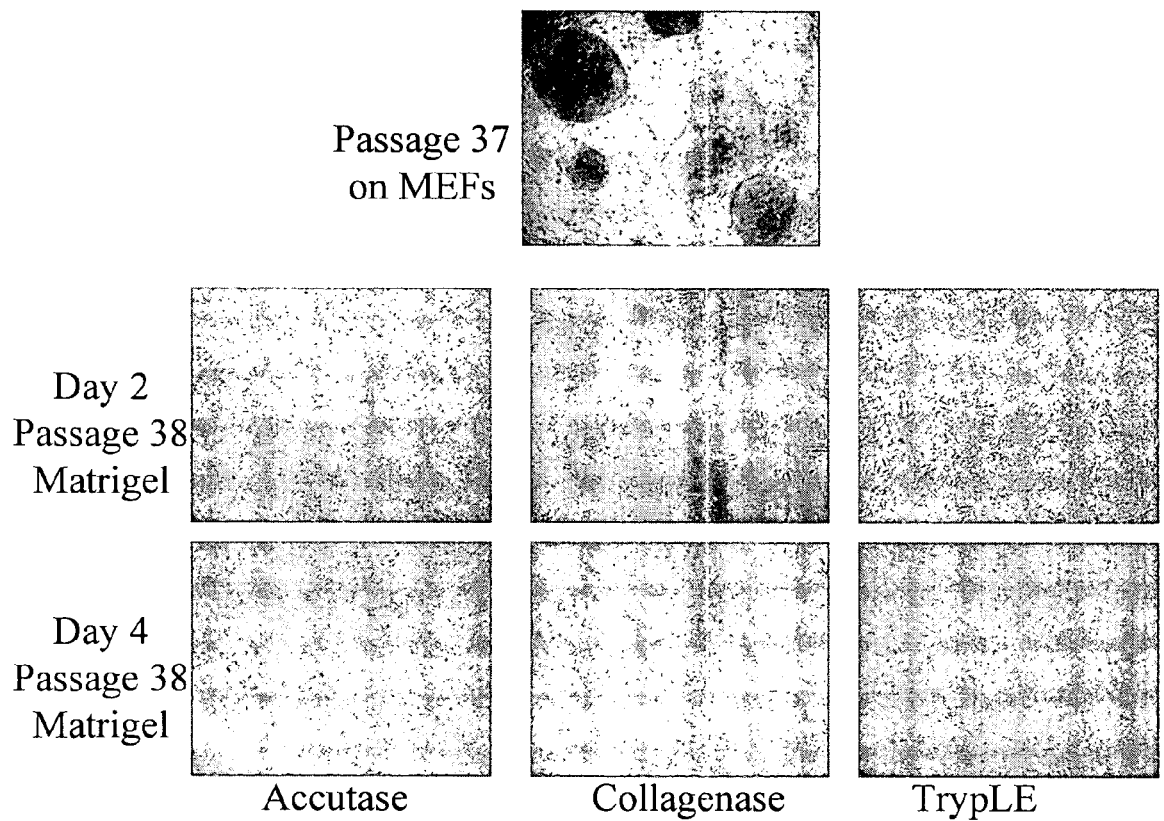
FIG. 13: Phase Micrographs of H1 hES cells grown on MEFs and then passaged to MATRIGEL™ as clusters or single cells. Passage 37 H1 hES cells passaged from MEFs to MATRIGEL™ with Collagenase form discrete, tightly packed colonies with some loose differentiated cells. H1 hES Cells passed once with Accutase™ or TrypLE™ form a monolayer culture with pockets of tightly packed differentiated cells.

Cells were maintained for 4 days with daily changes of MEF conditioned media supplemented with 16 µg/ml of bFGF. After 4 days in culture the cultures were confluent, and the single cell treated hES cells formed monolayers of hES cells with occasional pockets of fibroblasts, while the cluster passaged hES cells formed large colony style clusters of hES cells (FIG. 13). These cells were then passaged again.

As previously described, the cells were incubated in enzyme at 37° C. for 10 min. Accutase™ and TrypLE™ caused cells to lift from plastic and MATRIGEL™ after a 10-minute treatment. Collagenase did not lift cells, so cells were further incubated for 45 minutes in total at 37° C. The additional collagenase flask was lifted with Accutase™. The single cells were then with an Improved Neubauer hemocytometer.

Two ml of 2% Probumin in DMEM-F12 was then added to each flask after enzyme incubation, the total volume (~4 ml) from the flask was pipetted up and down 5-10 times in order to suspend as many cells as possible. The suspension was then transferred to a 50 ml conical tube and centrifuged for 5 min at 200×g. Cells were then resuspended in MEF conditioned media supplemented with 16 µg/ml of bFGF, and then plated to T25 flasks precoated with 1:30 MATRIGEL™ at a ratio of 1:4.

Accutase™ passaged cells, after four days in culture, had a density of 5.6 million cells total (223,000 cell/cm²), TrypLE™ passaged cells, after four days in culture, had a density of 5.05 million cells total (202,000 cell/cm²), and collagenase passaged cells, after four days in culture, had a density of 3.45 million cells total (138,000 cell/cm²). Given that the cells were passaged at a 1:4 ratio, the cells were plated at a density of 58,000 cell/cm² for Accutase™ passage, 51,000 cell/cm² for TrypLE™ passage, and 35,000 cell/cm².

Figure 14:
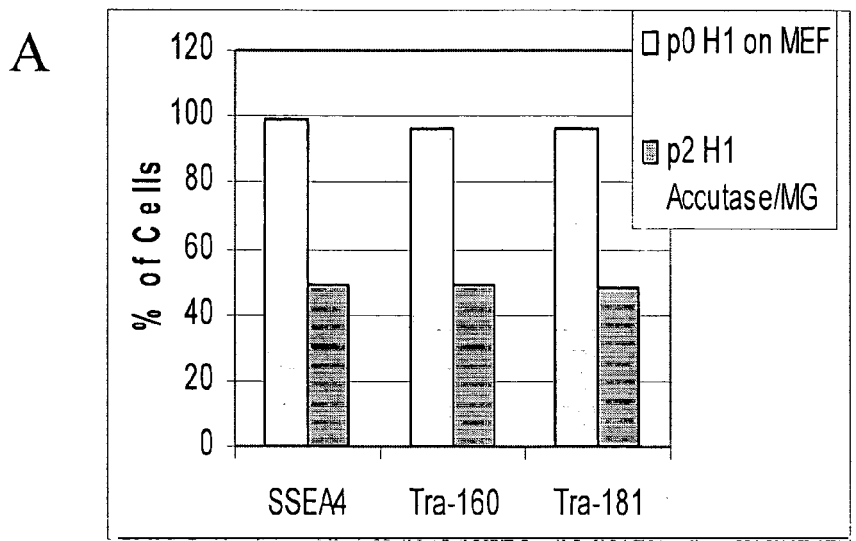
FIG. 14: H1 hES cells passaged directly to MATRIGEL™ from MEFS as single cells spontaneously differentiate. Panel A: The percentage of cells remaining in the population after two passages with Accutase™ from MEFs to MATRIGEL™. Panel B: Expression of markers of pluripotency and differentiation in hES cells after two passages with Accutase™ from MEFs to MATRIGEL™. Panel C: Phase Micrographs of H1 hES cells after two passages with Accutase™ from MEFs to MATRIGEL™.
Figure 14:
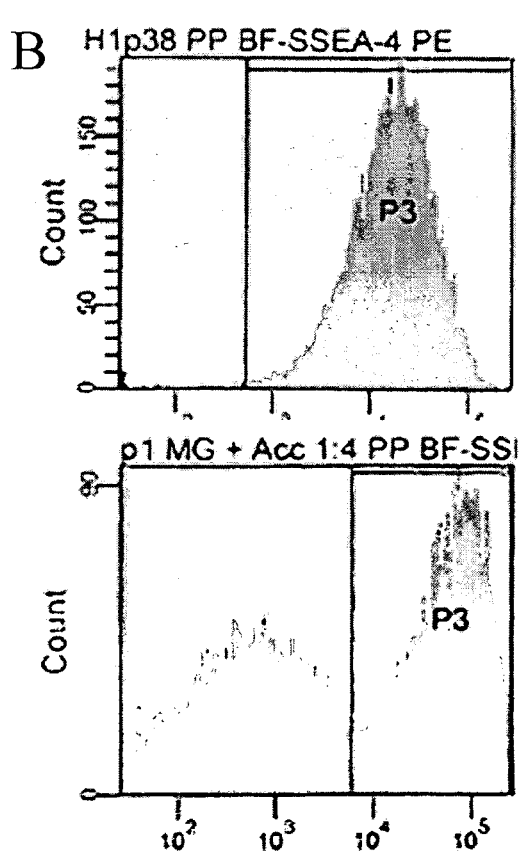
Figure 14:
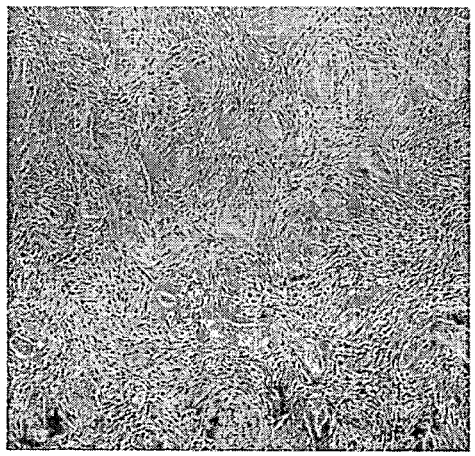

Cells were then grown for an additional 6 days, with daily media change of MEF conditioned media supplemented with 16 ng/ml of bFGF. While Cells passaged with collagenase form large colonies of dense and homogeneous cells and differentiated/fibroblast like cells are rare, cells passaged with Accutase™ or TrypLE™ grew very slowly, and over time stopped growing or were overgrown with fibroblast like cells that likely formed from differentiating hES cells (FIG. 14).

These results suggest that an intermediate stage of transition from feeders to feeder free (MATRIGEL™) culture using manual passage or enzyme which supports cluster style passage (collagenase or neutral protease) is best to acclimatize cells to feeder free culture on MATRIGEL™ before initiating single cell passage.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

What is claimed is:

1. A method for maintaining pluripotent stem cells, comprising the steps of:
   a) obtaining clusters of pluripotent stem cells;
   b) culturing the cluster of pluripotent stem cells in MEF-conditioned media;
   c) releasing the pluripotent stem cells as single cells with an enzyme; and
   d) plating the single pluripotent stem cells on a tissue culture substrate comprising an extracellular matrix, and either bFGF or fibroblast conditioned media;
   wherein the enzyme: (1) is TrypLE Select™ or TrypLE Express™; (2) is present in a concentration from about 0.5 g/l to about 2.5 g/l;
   wherein the enzyme is used to culture the cells for two minutes; and
   wherein there is no gain of chromosome abnormalities after releasing the cells.

2. The method of claim 1, wherein the pluripotent stem cells are released as single cells by treatment with the enzyme at a concentration of about 2.5 g/l.

3. The method of claim 1, wherein the pluripotent stem cells released as single cells are subsequently cultured with MEF-conditioned media.

4. The method of claim 1, wherein the tissue culture substrate is selected from the group consisting of matrigel, growth factor-reduced matrigel, fibronectin, laminin, human serum and collagen.

5. The method of claim 4, wherein the tissue culture substrate is growth factor-reduced matrigel.

6. The method of claim 5, wherein the growth factor-reduced matrigel is used at a dilution from about 1:30 to about 1:10.

7. The method of claim 6, wherein the growth factor-reduced matrigel is used at a dilution of 1:30.

8. The method of claim 1, wherein the pluripotent stem cells are embryonic stem cells.

9. The method of claim 8, wherein the embryonic stem cells are human.

10. A method for passaging pluripotent stem cells, comprising the steps of:
   a) obtaining clusters of pluripotent stem cells;
   b) culturing the cluster of pluripotent stem cells in MEF-conditioned media;
   c) releasing the pluripotent stem cells as single cells with an enzyme;
   d) plating the single pluripotent stem cells on a tissue culture substrate;
   e) allowing the single pluripotent stem cells to expand;

f) releasing the single pluripotent stem cells; and g) plating the single pluripotent stem cells on a new tissue culture substrate comprising an extracellular matrix, and either bFGF or fibroblast conditioned media;

wherein the enzyme: (1) is TrypLE Select™ or TrypLE Express™; (2) is present in a concentration from about 0.5 g/l to about 2.5 g/l;

wherein the enzyme is used to culture the cells for two minutes; and wherein there is no gain of chromosome abnormalities after releasing the cells.

11. The method of claim 10, wherein the pluripotent stem cells are released as single cells by treatment with the enzyme at a concentration of 2.5 g/l.

12. The method of claim 10, wherein the pluripotent stem cells released as single cells are subsequently cultured in MEF-conditioned media.

13. The method of claim 10, wherein the tissue culture substrate is selected from the group consisting of matrigel, growth factor-reduced matrigel, fibronectin, laminin, human serum and collagen.

14. The method of claim 13, wherein the tissue culture substrate is growth factor-reduced matrigel.

15. The method of claim 14, wherein the growth factor-reduced matrigel is used at a dilution from about 1:30 to about 1:10.

16. The method of claim 15, wherein the growth factor-reduced matrigel is used at a dilution of 1:30.

17. The method of claim 10, wherein the pluripotent stem cells are embryonic stem cells.

18. The method of claim 17, wherein the embryonic stem cells are human.

19. The method of claim 10, wherein the single pluripotent stem cells on a new tissue culture substrate are passaged onto another tissue culture substrate by releasing the cells and plating the released cells onto another tissue culture substrate.

20. A method for maintaining pluripotent stem cells, comprising the steps of:

a) obtaining clusters of pluripotent stem cells;

b) culturing the cluster of pluripotent stem cells in MEF conditioned media;

c) releasing the pluripotent stem cells as single cells with an enzyme; and d) plating the single pluripotent stem cells on a tissue culture substrate comprising an extracellular matrix, and MEF-conditioned media;

wherein the enzyme: (1) is TrypLE Select™ or TrypLE Express™; (2) is present in a concentration from about 0.5 g/l to about 2.5 g/l;

wherein the enzyme is used to culture the cells from two to five minutes; and wherein there is no gain of chromosome abnormalities after releasing the cells.

21. A method for passaging pluripotent stem cells, comprising the steps of:

a) obtaining clusters of pluripotent stem cells;

b) culturing the cluster of pluripotent stem cells in MEF conditioned media;

c) releasing the pluripotent stem cells as single cells with an enzyme; and d) plating the single pluripotent stem cells on a tissue culture substrate;

e) allowing the single pluripotent stem cells to expand;

f) releasing the single pluripotent stem cells; and g) plating the single pluripotent stem cells on a new tissue culture substrate comprising an extracellular matrix, and MEF-conditioned media;

wherein the enzyme: (1) is TrypLE Select™ or TrypLE Express™; (2) is present in a concentration from about 0.5 g/l to about 2.5 g/l;

wherein the enzyme is used to culture the cells from two to five minutes; and wherein there is no gain of chromosome abnormalities after releasing the cells.

22. The method of claim 1, wherein cell viability is at least 98% after releasing the cells.

23. The method of claim 10, wherein cell viability is at least 98% after releasing the cells.

24. The method of claim 20, wherein cell viability is at least 98% after releasing the cells.

25. The method of claim 21, wherein cell viability is at least 98% after releasing the cells.

* * * * *